US010246508B2

(12) United States Patent
Mor

(10) Patent No.: US 10,246,508 B2
(45) Date of Patent: Apr. 2, 2019

(54) ANTI EOTAXIN-2 ANTIBODIES THAT RECOGNIZE ADDITIONAL CCR3-BINDING CHEMOKINES

(71) Applicant: CHEMOMAB LTD., Tel Aviv (IL)

(72) Inventor: Adi Mor, Tel Aviv (IL)

(73) Assignee: CHEMOMAB LTD., Tel Aviv (IL)

( * ) Notice: Subject to any disclaimer, the term of this patent is extended or adjusted under 35 U.S.C. 154(b) by 108 days.

(21) Appl. No.: 15/122,241

(22) PCT Filed: Mar. 4, 2015

(86) PCT No.: PCT/IL2015/050234
§ 371 (c)(1),
(2) Date: Aug. 29, 2016

(87) PCT Pub. No.: WO2015/132790
PCT Pub. Date: Sep. 11, 2015

(65) Prior Publication Data
US 2016/0368979 A1 Dec. 22, 2016

Related U.S. Application Data

(60) Provisional application No. 61/947,852, filed on Mar. 4, 2014.

(51) Int. Cl.
C07K 16/24 (2006.01)
C07H 21/04 (2006.01)
C12N 15/85 (2006.01)
A61K 39/00 (2006.01)

(52) U.S. Cl.
CPC ........ *C07K 16/24* (2013.01); *A61K 2039/505* (2013.01); *A61K 2039/545* (2013.01); *C07K 2317/24* (2013.01); *C07K 2317/31* (2013.01); *C07K 2317/565* (2013.01); *C07K 2317/76* (2013.01); *C07K 2317/92* (2013.01)

(58) Field of Classification Search
CPC .......................... C07K 16/24; A61K 2039/505
See application file for complete search history.

(56) References Cited

FOREIGN PATENT DOCUMENTS

| WO | 00/27880 A2 | 5/2000 |
|---|---|---|
| WO | 2010/086854 A1 | 8/2010 |
| WO | 2011/025962 A1 | 3/2011 |

OTHER PUBLICATIONS

Goodnow et al, Cellular and genetic mechanisms of self tolerance and autoimmunity. Nature 2005; 2; 435 (7042):590-597.
Jose et al., Eotaxin: a potent eosinophil chemoattractant cytokine detected in a guinea pig model of allergic airways inflammation, J Exp Med 1994; 179: 881-887.
Kitaura et al., Molecular cloning of human eotaxin, an eosinophil-selective CC chemokine, and identification of a specific eosinophil eotaxin receptor, CC chemokine receptor 3, J Biol Chem 1996; 271: 7725-7730.
Ponath et al., Cloning of the human eosinophil chemoattractant, eotaxin. Expression, receptor binding, and functional properties suggest a mechanism for the selective recruitment of eosinophils. J Clin Invest 1996; 97: 604-612.
Bocchino et al., Eotaxin and CCR3 are up-regulated in exacerbations of chronic bronchitis, Allergy 2002; 57: 17-22.
Fulkerson et al,Targeting eosinophils in allergy, inflammation and beyond; Nat Rev Drug Discov. Feb. 2013;12 (2):117-129.
Amerio et al, Eotaxins and CCR3 receptor in inflammatory and allergic skin diseases: therapeutical implications. Curr Drug Targets Inflamm Allergy. 2003;2(1):81-94.
Pope et al,The eotaxin chemokines and CCR3 are fundamental regulators of allergen-induced pulmonary eosinophilia.J Immunol. 2005 15;175(8):5341-5350.
Ablin, Protective effect of eotaxin-2 inhibition in adjuvant-induced arthritis. Clin Exp Immunol. 2010 ;161(2):276-283.
Mausner et al, Eotaxin-2 blockade ameliorates experimental autoimmune encephalomyelitis World J Immunol 2013 27; 3(1): 7-14.
Gu et al, The immunobiology of systemic sclerosis. Semin Arthritis Rheum. Oct. 2008;38(2):132-160.
Bhattacharyya et al. Understanding fibrosis in systemic sclerosis: shifting paradigms, emerging opportunities Nat Rev Rheumatol. Oct. 25, 2011;8(1):42-54.
Dulkys et al. Detection of mRNA for eotaxin-2 and eotaxin-3 in human dermal fibroblasts and their distinct activation profile on human eosinophils.J Invest Dermatol. 2001, 116:498-505.
Huaux et al. Role of Eotaxin-1 (CCL11) and CC chemokine receptor 3 (CCR3) in bleomycin-induced lung injury and fibrosis. Am J Pathol. 2005;167(6):1485-1496.
Kohan et al. Eotaxin-2/CCL24 and eotaxin-3/CCL26 exert differential profibrogenic effects on humanlung fibroblasts, Ann Allergy Asthma Immunol. 2010; 104:66-72.
Baggiolini et al. Eotaxin: a VIC (very important chemokine) of allergic inflammation? 1996 J. Clin. Invest. 97:587.
Baggiolini et al. Human chemokines: an update.1997, Annu. Rev. Immunol. 15:675-705.
Noble et al. Pulmonary fibrosis: patterns and perpetrators. J Clin Invest 2012; 122: 2756-2762.
Maher, Beyond the diagnosis of idiopathic pulmonary fibrosis: the growing role of systems biology and stratified medicine. Curr Opin Pulm Med 2013; 19: 460-465.
Shimbori et al. Extracellular matrix microenvironment contributes actively to pulmonary fibrosis. Curr Opin Pulm Med 2013; 19: 446-452.
Raghu et al. An official ATS/ERS/JRS/ALAT statement: idiopathic pulmonary fibrosis: evidence-based guidelines for diagnosis and management. Am J Respir Crit Care Med 2011;183(6):788-824.

(Continued)

*Primary Examiner* — Ruixiang Li
(74) *Attorney, Agent, or Firm* — Vorys, Sater, Seymour and Pease LLP

(57) ABSTRACT

Provided are isolated polyspecific antibodies directed to a unique epitope in the chemokine eotaxin 2. The antibodies bind additional CCR3-binding chemokines. Further provided are methods for using of the antibodies for attenuating the migration of various cells and for treating fibrotic diseases, autoimmune inflammatory disorders, monocyte related disorders or allergic atopic disorders.

3 Claims, 21 Drawing Sheets
Specification includes a Sequence Listing.

(56) References Cited

OTHER PUBLICATIONS

Maher, Pirfenidone in idiopathic pulmonary fibrosis. Drugs Today 2010;46(7):473-482.
Bouros, Pirfenidone for idiopathic pulmonary fibrosis. Lancet 2011; 377(9779):1727-1729.
Taniguchi et al. Pirfenidone in idiopathic pulmonary fibrosis. Eur Respir J 2010; 35(4):821-829.
Eigenbort et al. Two-in-one antibodies with dual action Fabs. Current Opinion in Chemical Biology 2013, 17 (3):400-405.
Fagete et al. Dual Specificity of Anti-CXCL10-CXCL9 Antibodies Is Governed by Structural Mimicry. The Journal of Biological Chemistry 2011, 287(2):1458-1467.
Vangelista et al. Critical role of the N-loop and B1-strand hydrophobic clusters of RANTES-derived peptides in anti-HIV activity. Biochemical and Biophysical Research Communications 2006, 351(3):664-668.
Pakianathan et al. Distinct but Overlapping Epitopes for the Interaction of a CC-Chemokine with CCR1, CCR3, and CCR5. Biochemistry 1997, 36:9642-9648.

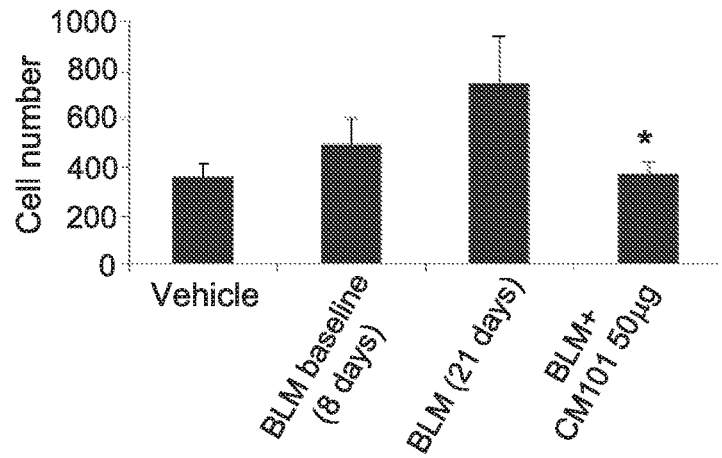
Fig. 5A
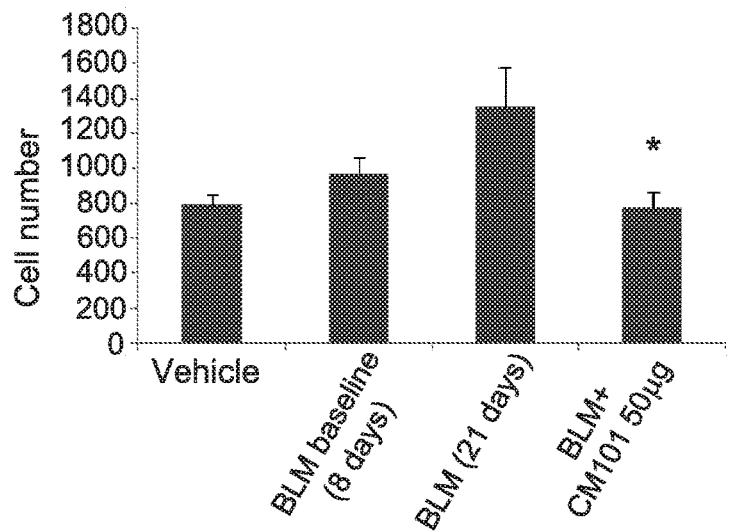
Fig. 5B
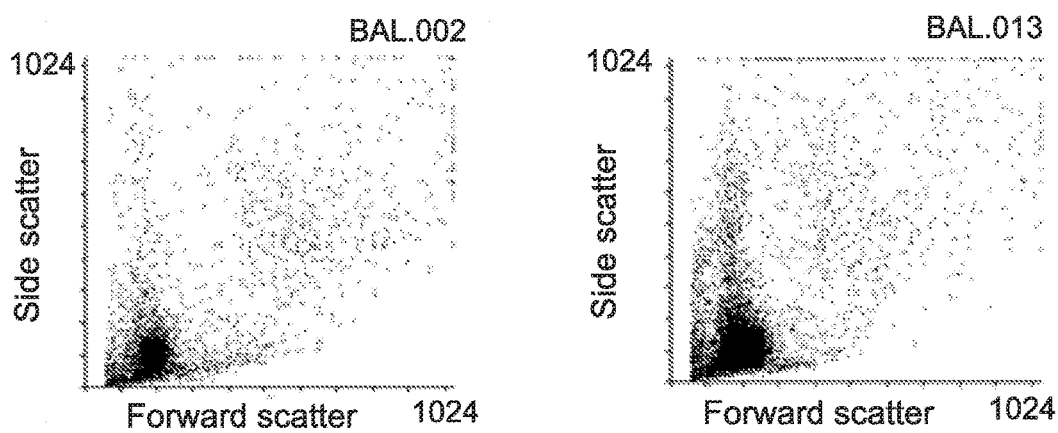
Fig. 5C
Fig. 5D

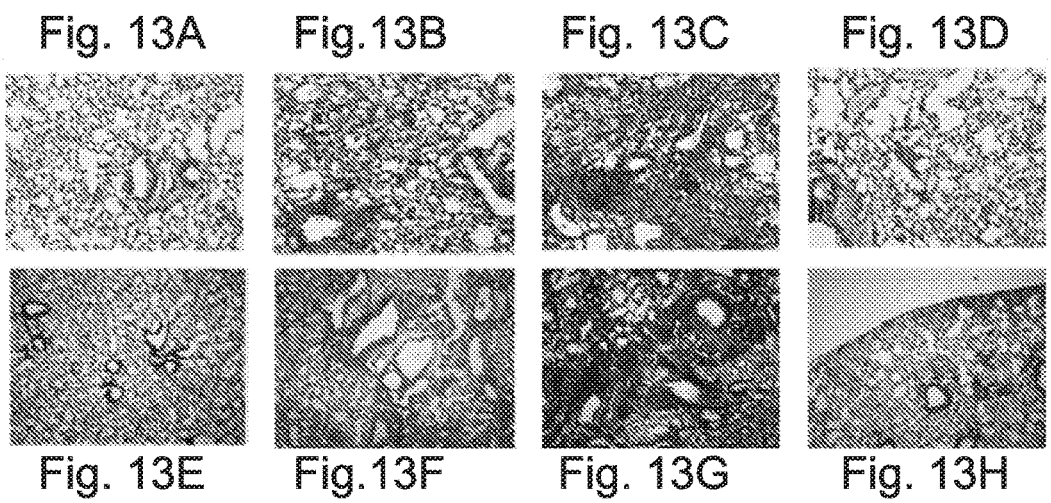
Fig. 13A  Fig. 13B  Fig. 13C  Fig. 13D
Fig. 13E  Fig. 13F  Fig. 13G  Fig. 13H
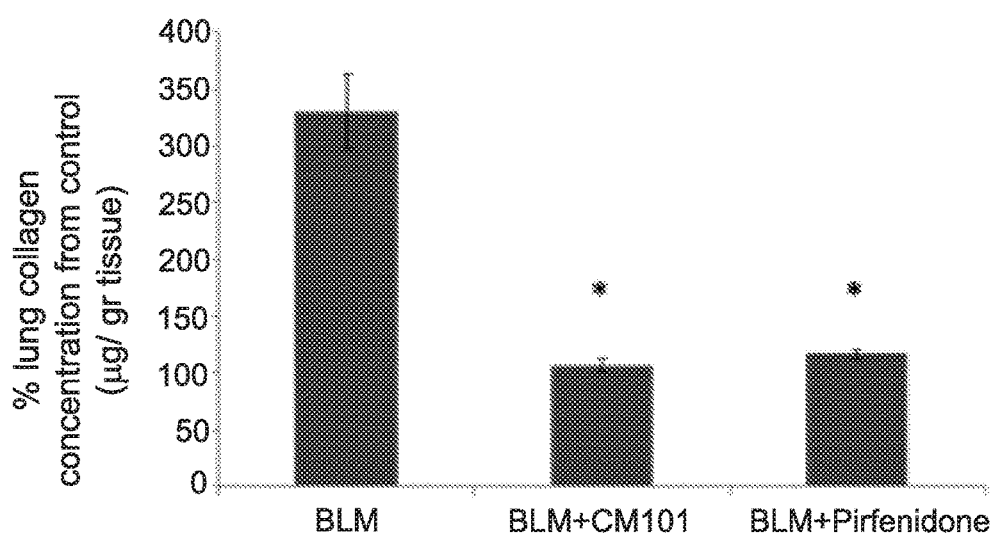
Fig. 14

| | | 10| | | | 20| | | | 30| | | | 40| |
|---|---|---|---|---|---|---|---|---|---|---|---|---|---|---|---|
| 1EIG_Eotaxin2 | - - V V I P S P | - C C M F F V S T R | I P E N R V V S Y Q L S S R - S T C L K |
| 1EOG_Eotaxin1 | - - G P A S V P T T | - C C F N L A N R K | I P L Q R L E S Y R R I T S - G K C P Q |
| 1B3A_Rantes | - - P Y S S D T T P | - C C F A Y I A R P | L P R A H I K E Y F Y T S G - K C S N |
| 1B00_MCP3 | Q P V G I N T S T T | - C C Y R F I N K K | I P L Q R L E S Y R R T T S - S H C P R |

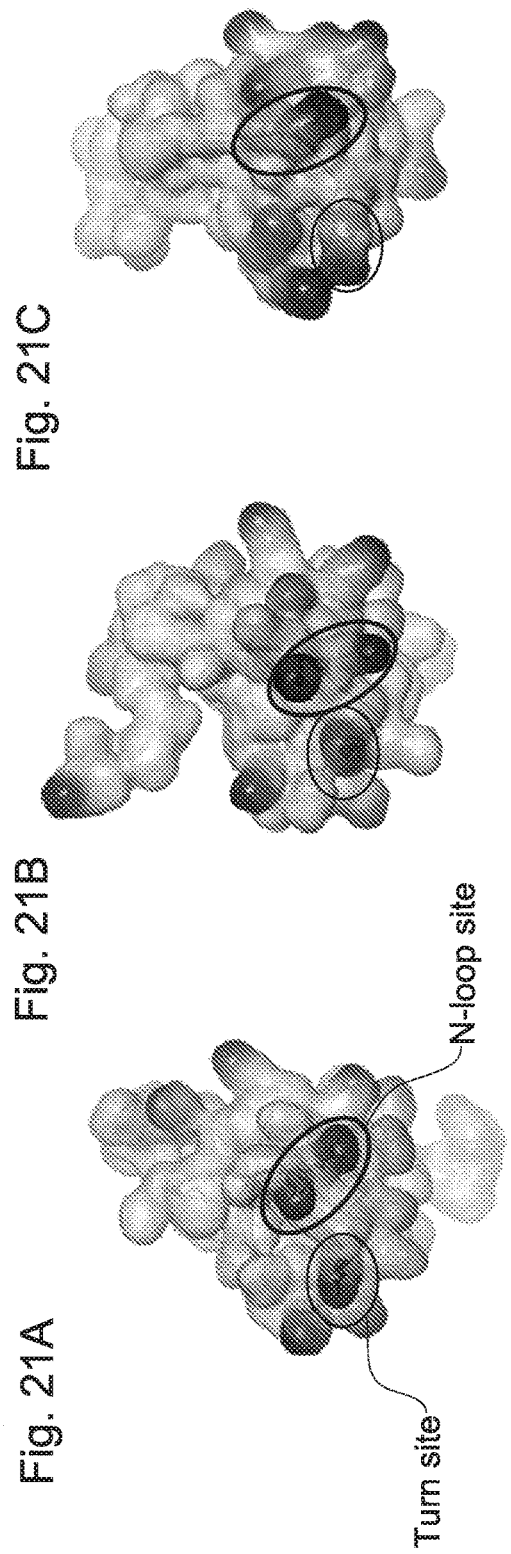

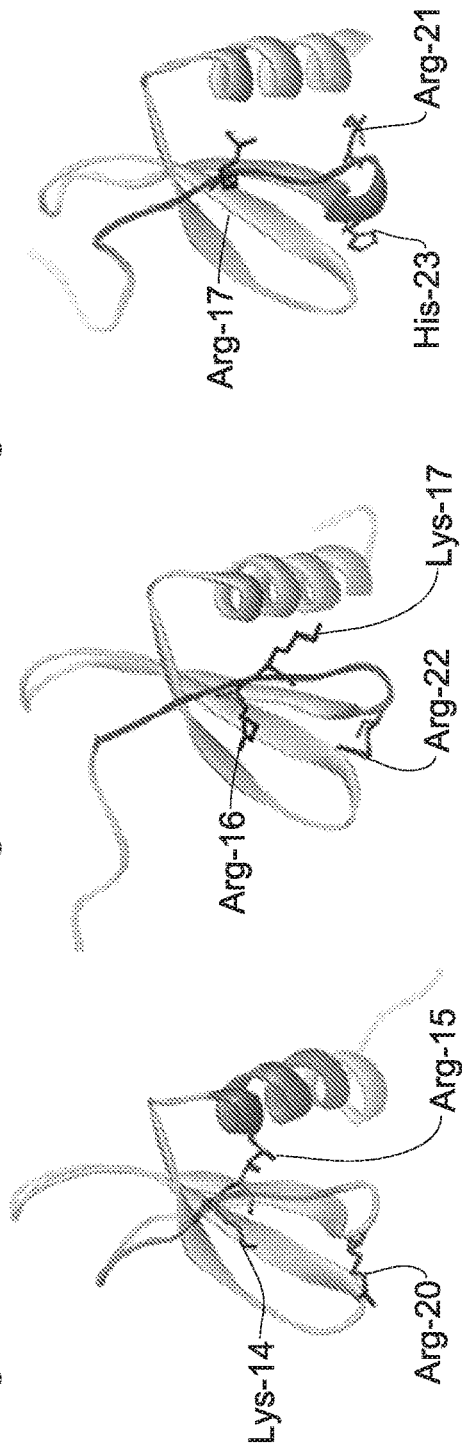
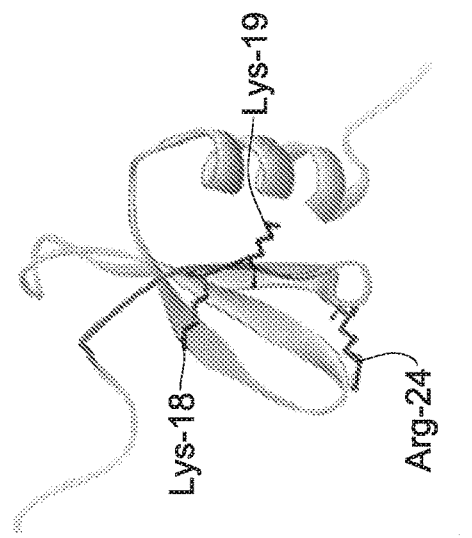
Fig. 21E    Fig. 21F    Fig. 21G    Fig. 21H

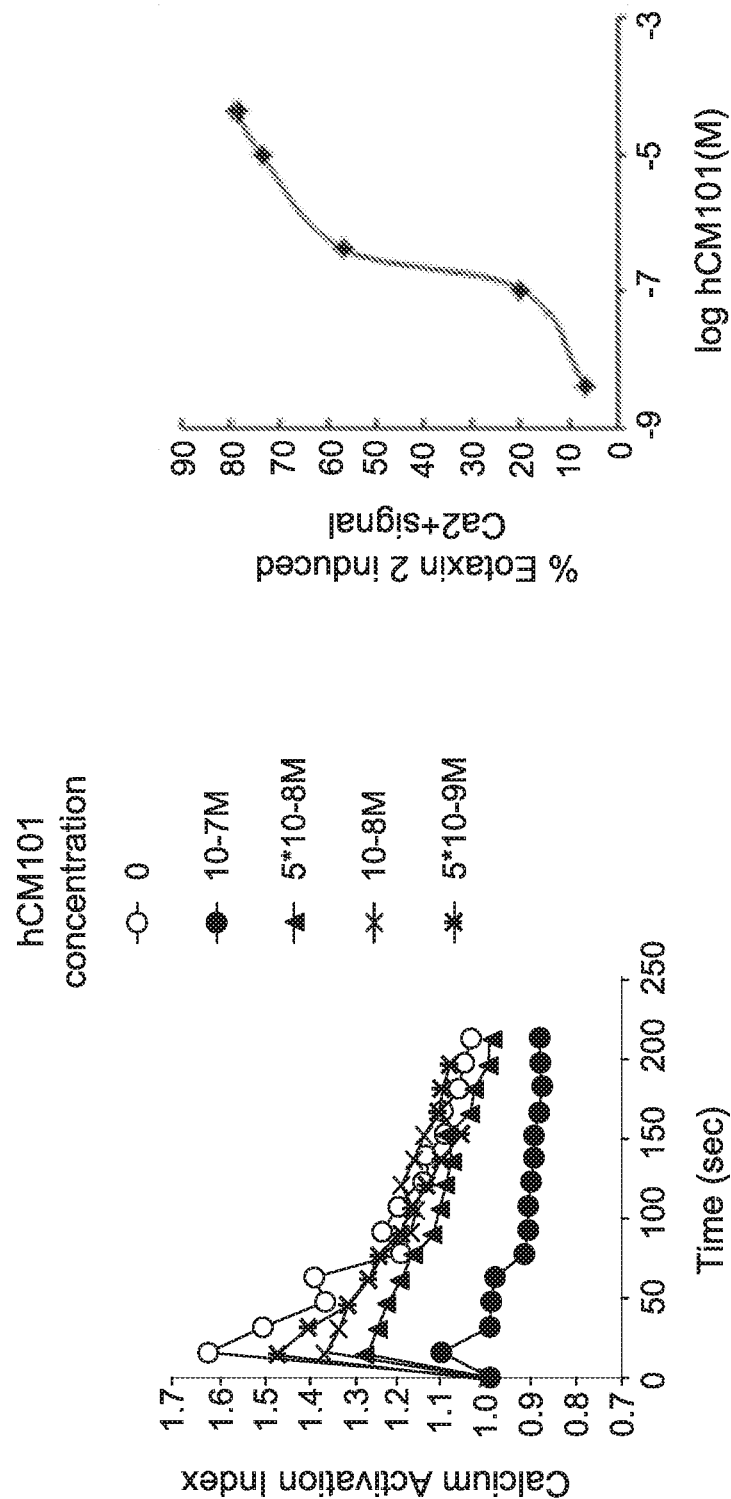

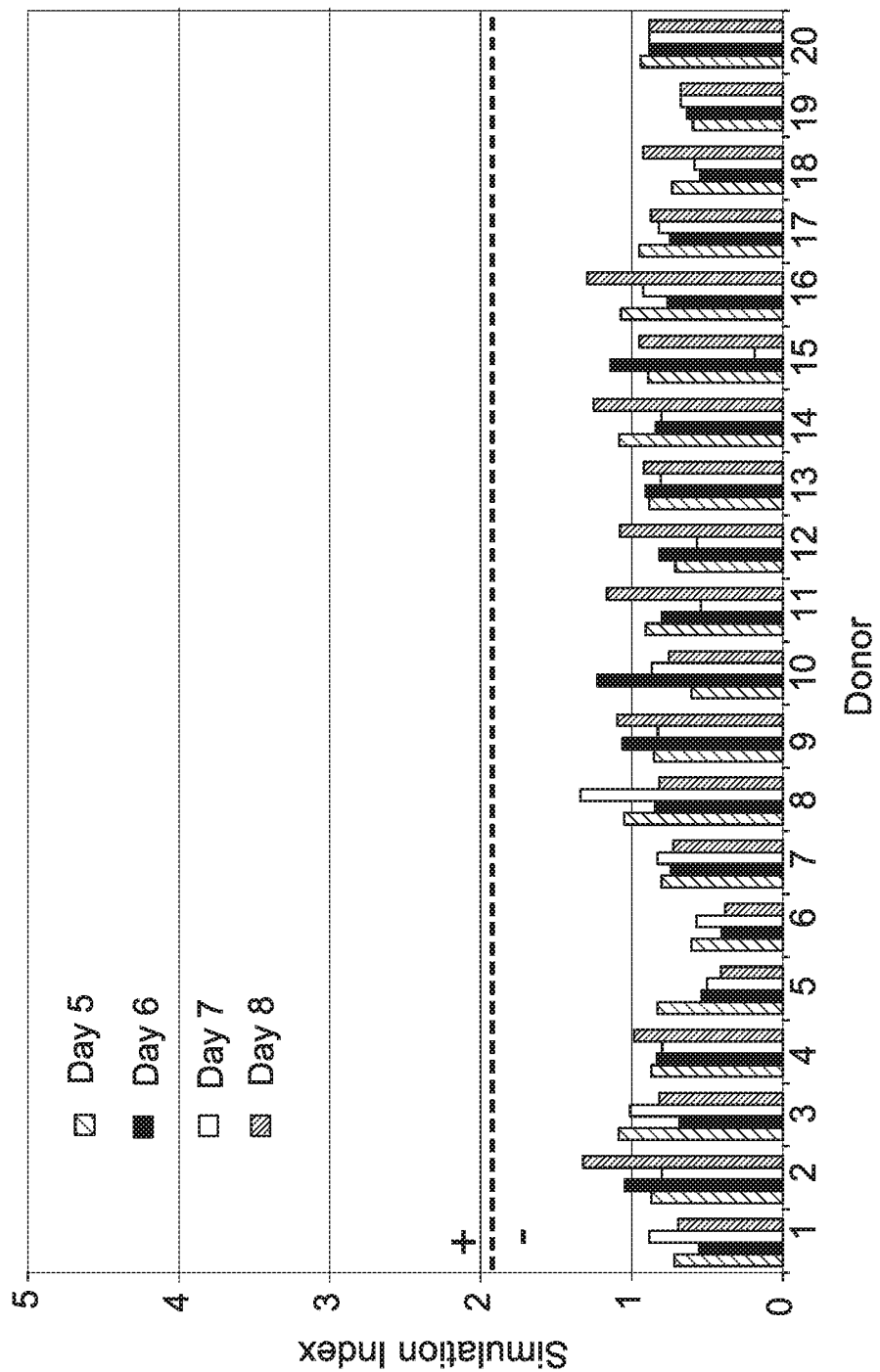

ANTI EOTAXIN-2 ANTIBODIES THAT RECOGNIZE ADDITIONAL CCR3-BINDING CHEMOKINES

The Sequence Listing submitted in text format (.txt) filed on Aug. 29, 2016, named "SequenceListing.txt", created on Jul. 14, 2016, 8.04 KB), is incorporated herein by reference.

FIELD OF INVENTION

The present invention concerns the use of anti eotaxin-2 (CCL24) monoclonal antibodies that possess poly-specific binding properties to other chemokines in the treatment of fibrotic, inflammatory, autoimmune and allergic diseases.

BACKGROUND OF INVENTION

Autoimmune disorders result from an overactive immune response of the body working against its own cells (1). Almost all autoimmune diseases are chronic and have no permanent cure. Over 300 million patients across the globe suffer from these disorders. Women constitute around 70%-75% of all autoimmune patients.

Eotaxin-2 is a chemokine that promotes cell trafficking and regulates inflammatory activities at the CCR3 gene complex site especially by inducing chemotaxis of eosinophils (2-4), basophils (4), and Th2-type lymphocytes (5).

So far, Eotaxin-2 was well known in the context of allergy. It was well documented that there is a significant increase in the levels of Eotaxin-2 during the allergic response (6-8). Recently, the inventors discovered that Eotaxin-2 is also involved in autoimmune and inflammatory diseases (WO 2010/086854) As described in Ablin et al. (9), inhibition of Eotaxin-2 demonsrated a protective effect in the Rat model of Rheumatod arthritis. In addition it was observed that Eotaxin-2 blockade attenuated experimental autoimmune encephalomyelitis as published by Mausner et al. (10).

Scleroderma, or systemic sclerosis (SSc), is a chronic, rare multisystem autoimmune disease characterized by immune system activation, endothelial dysfunction, and an active fibrotic process involving fibroblasts (11). The earliest stage in the development of the scleroderma lesions is endothelial cell activation and vascular damage. This is followed by the migration of inflammatory cells, primarily, monocytes and then lymphocytes. Eventually, a population of fibroblasts is activated. The activated fibroblasts continue to produce the extracellular matrix that underlies the ultimate fibrotic pathology of scleroderma (11). Studies revealed that human dermal fibroblasts express constitutively mRNA of the Eotaxin 1, 2 and 3 (13). In addition, elevated levels of Eotaxin were observed in lung fibrosis and in a bleomycine induced sclerosis mice model (14). Knockout mice to Eotaxin and CCR3 develop significantly reduced lung fibrosis (14, 15).

The proinflammatory CCR3 binding chemokines Eotaxin 1, Rantes and MCP-3 belong also to the CC chemokine family and serve as ligands to the CCR3 receptor. They are also involved in the migration of immune cells, a fact that explains their efficacy in inflammatory preclinical models (16, 17).

Idiopathic pulmonary fibrosis (IPF) is a progressive fibrotic disease limited to the lungs, occurring in older individuals, more frequently men, and characterized by a dismal prognosis, with a median survival of 3 to 5 years since diagnosis. The clinical features characterizing IPF include shortness of breath, radiographically evident diffuse pulmonary infiltrates, and varying degrees of inflammation, fibrosis, or both on biopsy. The cause of IPF remains unknown, however mechanisms underlying the recruitment and proliferation of fibroblasts and immune cells cells as well as their pathologic differentiation are thought to be a hallmark to disease progression. In addition, there appears to be a large number of mediators involved in IPF progress including cytokines, chemokines, fibrogenic factors, coagulant proteins, oxidants, and regulators of apoptosis (18, 19). It addition, the deposition of extracellular matrix components including collagen is integral to this fibrotic process (20).

Management of the disease generally includes some combination of supportive care, e.g, supplemental oxygen, pulmonary rehabilitation, consideration for lung transplant evaluation, and identification and treatment of possible comorbidities (21). Pirfenidone (Esbriet) and Nintedanib are the only FDA/EMA approved treatment currently available for individuals with IPF (22-24). Pirfenidone has antifibrotic and anti-inflammatory properties in various in vitro systems and animal models of fibrosis.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 2A is a graph showing the effect of treatment with anti-eotaxin-2 monoclonal antibody (CM101 in 10, 20 or 50 jag), IgG and PBS on the dermal thickness (±standard error). FIG. 2B is a graph showing the effect of treatment with anti-eotaxin-2 monoclonal antibody (CM101 in 10, 20 or 50 jag), IgG and PBS on the collagen concentration (±standard error), * indicates p≤0.05. (Vehicle—no treatment (PBS); BLM-bleomycin)

FIG. 5A-5B are graphs showing the effect of treatment with anti-eotaxin-2 monoclonal antibody (CM101, 50 µg) and PBS (vehicle) on mononuclear (FIG. 5A) and white blood cells (WBC) (FIG. 5B) infiltration within the bronchoalveolar fluid of mice in treatment mode (±standard error), *p≤0.05 (Vehicle—no treatment (PBS); BLM-bleomycin). FIGS. 5C-5F are representative FACS results (cell count within 30 sec in flow cytometry): 5C—PBS; 5D—BLM 8 days; 5E—BLM 21 days; 5F—BLM+CM101.

FIG. 6A—PBS; FIG. 6B—BLM baseline; FIG.

6C—BLM end; FIG. 6D mice treated with CM101 (treatment with CM 101 initiated after established disease).

FIG. 6E—PBS; FIG. 6F—BLM baseline; FIG. 6G—BLM end; FIG. 6H mice treated with CM101 (treatment with CM 101 initiated when experimental SSc is established).

FIG. 13A-13H are photographs showing representative appearance of lung lesions from mice treated with CM101 or PBS stained with hematoxylin eosin (H&E) (FIG. 13D and FIG. 13A, respectively) or with Masson's Trichrome staining (FIG. 13H and FIG. 13E, respectively). Lung lesions from mice treated with bleomycin (BLM) for the indicated number of days and stained with H&E appear in FIG. 13B and FIG. 13C. Lung lesions from mice treated with bleomycin (BLM) for the indicated number of days and stained with Masson's Trichrome staining appear in FIG. 13F and FIG. 13G.

FIG. 14 is a graph presenting the effect of CM101 (100 µg) compared to Pirfenidone (100 mg/kg/day) on lung collagen concentration of mice in IPF (±standard error). *$pv \leq 0.05$. (BLM-bleomycin).

FIG. 21A-21H are protein surface and ribbon diagram graphic representations of the epitope mapping representing the similar binding site of hCM101 to respectively Eotaxin 2 (FIG. 21A and FIG. 21E), eotaxin 1 (FIG. 21B and FIG. 21F), RANTES (FIG. 21C and FIG. 21G) and MCP3 (FIG. 21D and FIG. 21H). Protein surface is circled according to the charge; thick line represents positively charged area. The turn site is indicated by a circle and the N-loop site is indicated by an oval.

FIG. 29A shows 44% SMA positive cells in serum obtained from a scleroderma patient, FIG. 29B shows 22% SMA positive cells in serum obtained from a scleroderma patient treated with hCM101 (10 µg/ml) and FIG. 29C shows 27% SMA positive cells in serum obtained from a scleroderma patient treated with hCM101 (5 µg/ml).

FIG. 30A-30B are graphs presenting the time-resolved calcium activation index under influence of CM101 (100, 50, 10, 5, or 0 nM) (FIG. 30A) and variation in eotaxin 2 induced calcium signal as a function of CM101 concentration (FIG. 30B) in eosinophils. pv≤0.05 FIG. 31 is a graph presenting the proliferation of T cells following incubation with hCM101. The results are presented as stimulation index.

GENERAL DESCRIPTION

Figure 1A:
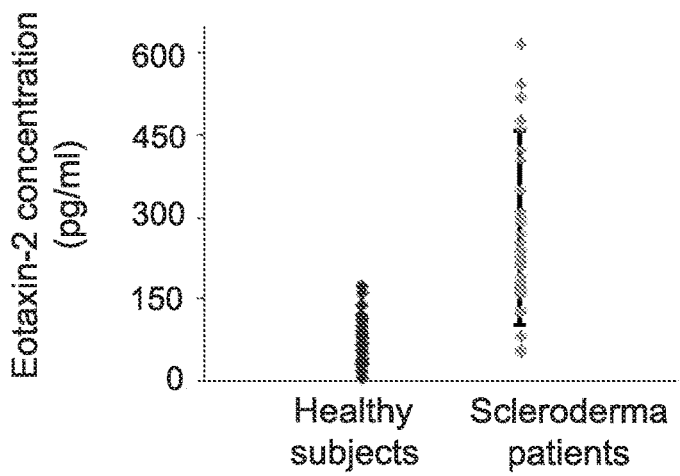
FIG. 1A-1C are graphs showing the circulating systemic levels of Eotaxin 2 (FIG. 1A), Rantes (FIG. 1B) and Eotaxin 1 (FIG. 1C) in systemic sclerosis patients as measured by Elisa. The results are presented in picograms per milliliter.

By one of its aspects the present invention provides an isolated polyspecific antibody, or any antigen-binding fragment thereof, that binds to at least two CCR3-binding chemokines for use in the treatment of fibrotic diseases, autoimmune inflammatory disorders, monocyte related disorders or allergic atopic disorders.

In some embodiments the antibody according to the invention is a monoclonal antibody. In other embodiments the monoclonal antibody according to the invention is a chimeric antibody, a human antibody, a humanized antibody or a fully humanized antibody.

In further embodiments the isolated polyspecific antibody for use according to the invention is wherein the antigen-binding fragment thereof is selected from the group consisting of Fv, single chain Fv (scFv), heavy chain variable region capable of binding the antigen, light chain variable region capable of binding the antigen, Fab, F(ab)$_2$' and any combination thereof.

In some embodiments the fibrotic disease as herein defined is selected from the group consisting of scleroderma, idiopathic pulmonary fibrosis (IPF), non alcoholic steathepatohepatitis (NASH), glomerulosclerosis, cirrhosis and metabolic syndromes.

In other embodiments the autoimmune inflammatory disorder as herein defined is selected from the group consisting of systemic lupus erythematosus (SLE), rheumatoid arthritis, psoriasis, colitis, uveitis, multiple sclerosis and type I diabetes.

In further embodiments the monocyte related disorder according to the invention is atherosclerosis.

In still further embodiments the allergic atopic disorder as herein deifned is selected from the group consisting of asthma, atopic dermatitis, urticaria and hypersensitivity reactions.

In some embodiments the isolated polyspecific antibody for use according to the invention is wherein the at least two CCR3-binding chemokines are selected from the group consisting of Eotaxin 1, Eotaxin-2, Rantes and MCP-3.

In other embodiments the isolated polyspecific antibody for use according to the invention is wherein the antibody binds Eotaxin 1, Eotaxin-2, Rantes and MCP-3.

In further embodiments the isolated polyspecific antibody for use as herein defined is wherein the antibody attenuates the migratory properties of CCR3, CCR1, CCR2 and CCR5 expressing cells.

In some embodiments the antibody as herein defined is a fully humanized antibody comprising a heavy chain variable region comprising:
  a) the complementary determining region VH CDR1 comprising the amino acid sequence denoted by SEQ ID NO. 5 or a variant thereof;
  b) the complementary determining region VH CDR2 comprising the amino acid sequence denoted by SEQ ID NO. 6 or a variant thereof; and
  c) the complementary determining region VH CDR3 comprising the amino acid sequence denoted by SEQ ID NO. 7 or a variant thereof; and a light chain variable region comprising
  d) the complementary determining region VK CDR1 comprising the amino acid sequence denoted by SEQ ID NO. 8 or a variant thereof;
  e) the complementary determining region VK CDR2 comprising the amino acid sequence denoted by SEQ ID NO. 9 or a variant thereof; and
  f) the complementary determining region VK CDR3 comprising the amino acid sequence denoted by SEQ ID NO. 10 or a variant thereof.

In other embodiments the antibody according to the invention is a fully humanized antibody comprising the heavy chain variable region denoted by SEQ ID NO:3 or a variant thereof and the light chain variable region denoted by SEQ ID NO: 4 or a variant thereof.

In another one of its aspects the present invention provides an isolated antibody that binds a conformational epitope in the N-loop region of a CCR3-binding chemokine, wherein said conformational epitope is characterized by a relatively high concentration of positive amino acid residues located between amino acid positions 14 and 24 in the amino acid sequence of said CCR3-binding chemokine.

In some embodiments the conformational epitope as herein defined comprises at least three positive amino acid residues between amino acid positions 14 and 24 in the amino acid sequence of said CCR3-binding chemokine.

In other embodiments the positive amino acid residues as herein defined are selected from the group consisting of Arg, Lys and His.

In further embodiments the conformational epitope as herein defined comprises an amino acid sequences selected from: the amino acid sequences denoted by SEQ ID NO: 15, SEQ ID NO: 16, SEQ ID NO: 17, SEQ ID NO: 18 or SEQ ID NO: 19.

By yet another one of its aspect the present invention provides an isolated polyspecific antibody, or any antigen-binding fragment thereof, that binds to at least two CCR3-binding chemokines, wherein said antibody is a fully humanized antibody and comprises a heavy chain variable region comprising:
  a) the complementary determining region VH CDR1 comprising the amino acid sequence denoted by SEQ ID NO. 5 or a variant thereof;
  b) the complementary determining region VH CDR2 comprising the amino acid sequence denoted by SEQ ID NO. 6 or a variant thereof; and
  c) the complementary determining region VH CDR3 comprising the amino acid sequence denoted by SEQ ID NO. 7 or a variant thereof; and a light chain variable region comprising
  d) the complementary determining region VK CDR1 comprising the amino acid sequence denoted by SEQ ID NO. 8 or a variant thereof;
  e) the complementary determining region VK CDR2 comprising the amino acid sequence denoted by SEQ ID NO. 9 or a variant thereof; and
  f) the complementary determining region VK CDR3 comprising the amino acid sequence denoted by SEQ ID NO. 10 or a variant thereof.

The present invention further provides a nucleic acid molecule encoding the antibody as herein defined.

By still another one of its aspects the present invention provides a nucleic acid molecule encoding a humanized antibody that binds to at least two CCR3-binding chemokines wherin said nucleic acid molecule comprises the sequence denoted by SEQ ID NO: 1 and SEQ ID NO: 2.

The present invention further provides an expression vector comprising the nucleic acid molecule according to the invention.

By yet another one of its aspects the present invention provides a host cell comprising the nucleic acid molecule according to the invention.

The present invention further provides a pharmaceutical composition comprising the antibody as herein defined and a pharmaceutically acceptable carrier.

In some embodiments the pharmaceutical composition according to the invention is for use in the treatment of fibrotic diseases, autoimmune inflammatory disorders, monocyte related disorders or allergic atopic disorders.

The present invention further provides a method of treating fibrotic diseases, autoimmune inflammatory disorders, monocyte related disorders or allergic atopic disorders comprising administering to a patient in need thereof a therapeutically acceptable amount of the antibody or the pharmaceutical composition as herein defined.

By still another one of its aspects the present invention provides a method of attenuating the migratory properties of CCR3, CCR1, CCR2 and CCR5 expressing cells in fibrotic diseases, autoimmune inflammatory disorders, monocyte related disorders or allergic atopic disorders comprising administering to a patient suffering of one of said diseases a therapeutically acceptable amount of the antibody or the pharmaceutical composition as herein defined.

The present invention further provides a method of screening and identifying antibodies capable of attenuating the migratory properties of at least one of CCR3, CCR1, CCR2 or CCR5 expressing cells, said method comprising:
  a. obtaining antibodies directed against a CCR3-binding chemokine; and
  b. assessing the binding of said antibodies to a conformational epitope in the N-loop region of a CCR3-binding chemokine, wherein said conformational epitope is characterized by a relatively high concentration of positive amino acid residues located between amino acid positions 14 and 24 in the amino acid sequence of said CCR3-binding chemokine;
  c. selecting antibodies which bind to said conformational epitope;
    wherein antibodies that bind specifically to said conformational epitope are capable of efficiently attenuating the migratory properties of CCR3, CCR1, CCR2 and CCR5 expressing cells.

In some embodiments the method of screening and identifying antibodies capable of attenuating the migratory properties of at least one of CCR3, CCR1, CCR2 or CCR5 expressing cells is wherein said conformational epitope comprises an amino acid sequence selected from the group consisting of the amino acid sequences denoted by SEQ ID NO: 15, SEQ ID NO: 16, SEQ ID NO: 17, SEQ ID NO: 18 and SEQ ID NO: 19.

In another aspect, the present invention provides an isolated N-loop region of a CCR3-binding chemokine comprising a conformational epitope, wherein said conformational epitope is characterized by a relatively high concentration of positive amino acid residues located between amino acid positions 14 and 24 in the amino acid sequence of said CCR3-binding chemokine, for generating antibodies against said CCR3-binding chemokine.

In certain embodiments said isolated N-loop region comprises an amino acid sequence selected from the group consisting of the amino acid sequences denoted by SEQ ID NO: 15, SEQ ID NO: 16, SEQ ID NO: 17, SEQ ID NO: 18 and SEQ ID NO: 19.

DETAILED DESCRIPTION OF THE INVENTION

The present invention is based on the surprising finding that an antibody directed to a conformational epitope in the eotaxin 2 (CCL24) polypeptide binds and inhibits the activity of eotaxin 2 as well as additional chemotactic agents, the proinflammatory CCR3 binding chemokines: Eotaxin 1, Rantes and MCP-3. The present invention thus provides a unique fully humanized monoclonal antibody (termed herein hCM101) capable of preventing the migration of immune cells by neutralizing at least one of the chemokines responsible for their chemotaxis. The antibody hCM101 inhibits the binding of these CCR3-bindnig chemokines (some of which bind additional receptors) to their respective receptors and functionally attenuates the migratory properties of CCR3, CCR1, CCR2 and CCR5 expressing cells (eosinophil and monocytic cell lines as well as human fibroblasts).

Without wishing to be bound by theory, these unique, exceptional properties of the antibody being polyspecific, namely, targeting several chemokines, may explain its efficacy and its potential ability to overcome redundancy in chemokine functions. As such, this antibody may be useful in the treatment of autoimmune diseases which are associated with chronic inflammation and characterized by the migration and infiltration of immune cells, including allergic and fibrotic diseases.

The present invention thus provides an isolated polyspecific antibody, or any antigen-binding fragment thereof, that binds to at least two CCR3-binding chemokines for use in the treatment of fibrotic diseases, autoimmune inflammatory disorders, monocyte related disorders or allergic atopic disorders.

As used herein the term "poly-specific (or polyspecific) antibody" refers to poly reactive antibodies which are able to recognize multiple antigens, specifically the invention encompasses poly-specific antibodies which are able to recognize several, different, proinflammatory CCR3-binding chemokines. The antibody of the invention was generated against eotaxin 2 and was found subsequently to bind and effectively attenuate the activity of additional chemokines (for example, eotaxin 1, Rantes and MCP-3). In certain embodiments, the poly-specific antibody of the invention binds to the various chemokines with similar affinities. In other embodiments, the antibody has differential binding affinity to the various chemokines. In one specific embodiment the antibody binds with a higher affinity to eotaxin 2 than to the other tested chemokines. Apparently, the poly-specific antibodies of the invention recognize a cross-reactive epitope in these proinflammatory CCR3-binding chemokines.

CCR3 (C—C chemokine receptor type 3) is a protein that in humans is encoded by the CCR3 gene. CCR3 has also recently been designated CD193 (cluster of differentiation 193). The protein encoded by this gene is a receptor for C—C type chemokines. It is a 7-transmembrane G protein-coupled receptor which is expressed by eosinophils as well as by a wide array of cell types including macrophages and endothelial cells. This receptor binds and responds to a variety of chemokines, including eotaxin (also termed eotaxin 1 or CCL11), eotaxin-2 (CCL24), eotaxin-3 (CCL26), MCP-3 (CCL7), MCP-4 (CCL13), and RANTES (CCL5).

The term "CCR3-binding chemokines" as herein defined refers to any chemokine that binds to the protein CCR3 and encompasses for example but not limited to Eotaxin 1, Eotaxin-2, Eotaxin-3, Rantes, MCP-3 and MCP-4. It should be emphasized that some of the CCR3-binding chemokines also bind additional chemokine receptors, e.g. CCR1, CCR2 or CCR5.

Thus in some embodiments, the isolated polyspecific antibody for use of the invention is wherein the at least two CCR3-binding chemokines are selected from the group consisting of Eotaxin 1, Eotaxin-2, Rantes and MCP-3.

The terms "eotaxin 2" (eosinophil chemotactic protein 2), "CCL24" (Chemokine (C—C motif) ligand 24) or "MPIF-2" (myeloid progenitor inhibitory factor 2) are used interchangeably and refer to a cytokine belonging to the CC chemokine family which is encoded by the human CCL24 gene, located on human chromosome 7. CCL24 interacts with chemokine receptor CCR3. CCL24 activity includes induction of chemotaxis in eosinophils, basophils, T lymphocytes and neutrophils, as well as induction of angiogenic and migratory responses in endothelial and smooth muscle cells. The amino acid sequence of eotaxin 2 (without the N-terminal signal peptide) is denoted by SEQ ID NO: 11.

As indicated above, additional CCR3-binding chemokines encompassed by the present invention are Eotaxin 1, Eotaxin-3, Rantes, MCP-3 and MCP-4, to name but a few.

The term "Eotaxin 1" (also known as C—C motif chemokine 11 and eosinophil chemotactic protein) as herein defined refers to a protein that in humans is encoded by the CCL11 gene. Eotaxin 1 selectively recruits eosinophils by inducing their chemotaxis, and therefore, is implicated in allergic responses. The effects of Eotaxin 1 are mediated by its binding to a G-protein-linked receptor known as a chemokine receptor, including CCR2, CCR3 and CCR5. The amino acid sequence of human Eotaxin 1 (without the N-terminal signal peptide) is denoted for example by SEQ ID NO: 12.

The term "Rantes" (regulated on activation, normal T cell expressed and secreted), also termed chemokine (C—C motif) ligand 5 (CCL5) as herein defined refers to a protein which in humans is encoded by the CCL5 gene. Rantes is an 8 kDa protein classified as a chemotactic cytokine or chemokine for T cells, eosinophils, and basophils, and plays an active role in recruiting leukocytes into inflammatory sites. With the help of particular cytokines (i.e., IL-2 and IFN-gamma) that are released by T cells, Rantes also induces the proliferation and activation of certain natural-killer (NK) cells to form CHAK (CC-Chemokine-activated killer) cells. Rantes binds, inter alia, the CCR3 receptor. The amino acid sequence of human Rantes (without the N-terminal signal peptide) is denoted for example by SEQ ID NO: 13.

The term "MCP-3" (monocyte-specific chemokine 3) also termed chemokine (C—C motif) ligand 7 (CCL7) as herein defined is classified among the subfamily of chemokines known as CC chemokines. MCP-3 specifically attracts monocytes, and regulates macrophages function. It is produced by certain tumor cell lines and by macrophages. This chemokine is located on chromosome 17 in humans, in a large cluster containing many other CC chemokines. Rantes binds, inter alia, the CCR3 receptor. The amino acid sequence of human MCP-3 (without the N-terminal signal peptide) is denoted for example by SEQ ID NO: 14.

In some embodiments the isolated polyspecific antibody for use of the invention is wherein the antibody binds Eotaxin 1, Eotaxin-2, Rantes and MCP-3.

In other specific embodiments the isolated polyspecific antibody for use of the invention attenuates the migratory properties of CCR3, CCR1, CCR2 and CCR5 expressing cells.

By the term "attenuates the migratory properties" of CCR3, CCR1, CCR2 and CCR5 expressing cells it is meant that the antibody of the invention reduces cell migration as can be measured in a chemotaxis assay. Such chemotaxis assays are well known in the art. Exemplary chemotaxis assays are shown in the Examples section below. Attenuation of migratory properties means any statistically significant reduction in cell migration as compared with non-treated cells. For example, a reduction of at least 50% in the number of migrating cells.

As exemplified in the Examples section below the antibody of the invention is capable of binding to several proinflammatory chemokines and to inhibit their various activities, such as inhibition of cell recruitment or chemotaxis (for example recruitment or chemotaxis of eosinophils or monocytes or fibroblasts), inhibition of the transition of fibroblasts to myoblasts, as well as reduction of cellular activation. As such these antibodies can be useful in the treatment of diseases whose detrimental symptoms or effects are mediated at least partly by proinflammatory CCR3 chemokines.

Specifically, as shown in the examples below, the antibody of the invention caused a significant decrease in several features in models of idiopathic pulmonary fibrosis (IPF) and scleroderma, which are classified as fibrotic diseases.

Fibrosis is the formation of excess fibrous connective tissue in an organ or tissue in a reparative or reactive process. This can be a reactive, benign, or pathological state. Fibrosis can be used to describe the pathological state of excess deposition of fibrous tissue, as well as the process of connective tissue deposition in healing. Thus as used herein the term "fibrotic disease" relates to an abnormal condition in which fibrous connective tissue spreads over or replaces normal smooth muscle or other normal organ tissue. Fibrosis can involve the heart, lung, peritoneum, skin or kidney. Non-limiting examples of a fibrotic disease include scleroderma, idiopathic pulmonary fibrosis (IPF) non alcoholic steathepatohepatitis (NASH), glomerulosclerosis, cirrhosis and metabolic syndromes.

Thus in some embodiments the fibrotic disease is selected from the group consisting of scleroderma, idiopathic pulmonary fibrosis (IPF), non alcoholic steathepatohepatitis (NASH), glomerulosclerosis, cirrhosis and metabolic syndromes.

The term "Scleroderma" also known as systemic sclerosis as herein defined refers to a chronic systemic autoimmune disease characterised by hardening (sclero) of the skin (derma). In the more severe form, it also affects internal organs. Scleroderma can be limited scleroderma and involve cutaneous manifestations that mainly affect the hands, arms and face or diffuse scleroderma, which is rapidly progressing and affects a large area of the skin and one or more internal organs, frequently the kidneys, esophagus, heart and/or lungs. This form of scleroderma can be quite disabling. There are no treatments for scleroderma itself, but individual organ system complications are treated.

The term "idiopathic pulmonary fibrosis" (IPF) refers to progessive fibrosis of the pulmonary alveolar walls, with progressive dyspnea and potentially fatal lack of oxygen or right heart failure. The acute form is called Hamman-Rich syndrome.

As used herein the term "inflammation" refers to the complex biological response of the immune system to harmful stimuli, such as pathogens, damaged cells (caused by e.g. burns, trauma, neoplasma) or irritants such as chemicals, heat or cold. The term "inflammatory disease" or "inflammatory disorder" refers to diseases associated with inflammation, including, but not limited to autoimmune inflammatory disorders.

As used herein the term Autoimmune disease describes a pathological condition resulting from an overactive immune response of the body against substances and tissues normally present in the body. The immune system mistakes some part of the body as a pathogen and attacks it. This may be restricted to certain organs or involve a particular tissue in different places which may affect the basement membrane in both the lung and the kidney. Examples of autoimmune diseases include rheumatoid arthritis, multiple sclerosis, coeliac disease, Diabetes Mellitus type I (IDDM), systemic lupus erythematosus (SLE), Sjogren's syndrome, Churg-Strauss Syndrome, Hashimoto's thyroditis, Graves' disease, psoriasis, inflammatory bowel disease (ulcerative colitis and Crohn's disease), scleroderma and pemphigus.

As used herein the term "autoimmune inflammatory disorders" relates to disorders resulting from the immune system attacking the body's own tissues that are also characterized by increased inflammation. Non-limiting examples of an autoimmune inflammatory disorder include systemic lupus erythematosus (SLE), rheumatoid arthritis, psoriasis, colitis, uveitis, multiple sclerosis and type I diabetes.

Therefore in some embodiments the autoimmune inflammatory disorder as herein defined is selected from the group consisting of systemic lupus erythematosus (SLE), rheumatoid arthritis, psoriasis, colitis, uveitis, multiple sclerosis and type I diabetes.

As used herein the term "monocyte related disorder" relates to genetic abnormalities that affect the function of monocytes and macrophages and cause buildup of debris within the cells resulting for example in the lipid storage diseases (such as Gaucher disease and Niemann-Pick disease) or in atherosclerosis. An increase of monocytes in the blood (monocytosis) occurs in response to chronic infections, in autoimmune disorders, in blood disorders, and in certain cancers. A proliferation of macrophages in tissues can occur in response to infections, sarcoidosis, and Langerhans cell histiocytosis.

In further embodiments the monocyte related disorder accoridng to the present invention is atherosclerosis.

As used herein the term "atherosclerosis" (also known as Arteriosclerotic Vascular Disease or ASVD) is a pathological condition in which an artery wall thickens as the result of a build-up of fatty materials such as cholesterol. This process is a result of a chronic inflammatory response in the walls of arteries, in large part due to the accumulation of macrophages and promoted by low-density lipoproteins without adequate removal of fats and cholesterol from the macrophages by functional high density lipoproteins (HDL). This hardening or furring of the arteries is caused by the formation of multiple plaques within the arteries.

As used herein the term "allergic atopic disorder" relates to a form of allergy that afflicts persons with a genetic predisposition to hypersensitivity to certain allergens. Non-limiting examples of an allergic atopic disorder include asthma, atopic dermatitis, hay fever urticaria and hypersensitivity reactions.

Thus in still further embodiments, the allergic atopic disorder according to the invention is selected from the group consisting of asthma, atopic dermatitis, urticaria and hypersensitivity reactions.

As indicated above, the present invention provides isolated poly-specific antibodies that bind to at least two proinflammatory CCR3-binding chemokines. The term "antibody" refers to a polypeptide encoded by an immunoglobulin gene or functional fragments thereof that specifically bind and recognize an antigen, namely proinflammatory CCR3-binding chemokines. Specifically, the antibody of the invention binds and recognizes at least eotaxin 2, eotaxin 1, RANTES and MCP-3.

In a preferred embodiment the antibody of the invention is a monoclonal antibody. The term "monoclonal antibody", "monoclonal antibodies" or "mAb" as herein defined refers to a population of substantially homogenous antibodies, i.e., the individual antibodies comprising the population are identical except for possibly naturally occurring mutations that may be present in minor amounts. Monoclonal antibodies are directed against a single antigenic site.

Monoclonal antibodies may be prepared and purified by any method known in the art. For example, monoclonal antibodies may be prepared from B cells taken from the spleen or lymph nodes of immunized animals (e.g. rats or mice), by fusion with immortalized B cells under conditions which favor the growth of hybrid cells.

Immunization of mice may be carried out for example as described in WO 2010/086854. Briefly, immunization of mice may be carried out for example by primary subcutaneous (s.c.) immunization with the desired antigen, namely with a CCR3-binding chemokine, e.g. eotaxin 2, or with a fragment of a CCR3-binding chemokine comprising a conformational epitope in the N-loop (e.g. 50 µg) emulsified with complete Freund's adjuvant. Two subcutaneous booster injections with the antigen (e.g. 50 µg) emulsified with incomplete Freund's adjuvant are then administered every 2 weeks. The mice with the highest neutralizing antibody titer receive an additional intravenous (i.v.) boost of the antigen (e.g. 5 µg) in PBS four days prior to spleen removal.

After the final boost (e.g. four days), the spleen of the mouse with the highest neutralizing antibody titer is removed and splenocytes are fused to mouse myeloma cells (e.g. NSO cells) using polyethylene glycol, as previously described (Köhler, G. and Milstein, C. (1975) Nature 256: 495-497). After fusion, the hybridoma cells are selected by growing the cells in HAT (hypoxantine-aminopterin-thymidine) medium. Cell clones are then screened for specific antibody production, for example using the ELISA assays described below.

Purification of monoclonal antibodies may be based for example on affinity chromatography, namely, using an affinity column to which the specific epitope is conjugated.

An exemplary antibody structural unit comprises a tetramer, as known in the art. Each tetramer is composed of two identical pairs of polypeptide chains, each pair having one "light chain" and one "heavy chain". The N-terminus of each chain defines a variable region of about 100 to 110 or more amino acids primarily responsible for antigen (or epitope) recognition. Thus, the terms "heavy chain variable region" ($V_H$) and "light chain variable region" ($V_L$) refer to these heavy and light chains, respectively. More specifically, the variable region is subdivided into hypervariable and framework (FR) regions. Hypervariable regions have a high ratio of different amino acids in a given position, relative to the most common amino acid in that position. Four FR regions which have more stable amino acids sequences separate the hypervariable regions. The hypervariable regions directly contact a portion of the antigen's surface. For this reason, hypervariable regions are herein referred to as "complementarity determining regions", or "CDRs".

From N-terminal to C-terminal, both light and heavy chains comprise the domains FR1, CDR1, FR2, CDR2, FR3, CDR3 and FR4. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located.

Thus, the complementarity determining regions CDRH1, CDRH2 and CDRH3 refer to the three complementarity determining regions starting from the N-terminus of the antibody's heavy chain and the complementarity determining regions CDRL1, CDRL2 and CDRL3 refer to the three complementarity determining regions starting from the N-terminus of the antibody's light chain.

In some embodiments the isolated poly-specific monoclonal antibody according to the invention is a chimeric antibody, a human antibody, a humanized antibody or a fully humanized antibody.

The term "chimeric" antibodies as herein defined refers to antibodies in which a portion of the heavy and/or light chain is derived from a particular species, while the remainder of the chain(s) is derived from another species, as well as fragments of such antibodies, which exhibit the same biological activity.

Chimeric antibodies may be prepared by any method known in the art, for example as described below.

A murine-human chimeric antibody may be prepared by the amplification and cloning of murine $V_H$ and $V_L$ genes, encoding the antibody variable regions, followed by murine-human chimeric antibody expression. To this end, total RNA is isolated from murine anti-eotaxin 2 hybridoma cells that are shown to secrete antibodies with the desired characteristics and cDNA is synthesized using oligo $(dT)_{15}$ primer, M-MLV and AMV reverse transcriptases. Amplification of the heavy and the light variable genes ($V_H$ and $V_L$) may be carried out using a panel of primers directed at the 5' terminus of framework 1 of each gene, essentially as described in Benhar and Reiter (Benhar, I. and Reiter, Y. (2002) Curr. Protoc. Immunol. Chapter 10: Unit 10 19B), and to the constant region ($C_H1$ or $C_k$, respectively) at the 3' end.

The variable genes are then re-amplified using non-degenerate primers introducing restriction sites at both ends for cloning, foe example, into a pCMV-based antibody expression vector.

The amplified heavy and light variable genes are separately purified, digested and cloned into appropriate mammalian full-length Ig expression vectors, providing each chain with a corresponding signal-peptide and constant gene, resulting in IgG1/k murine human chimeric antibody expression.

For preparing large quantities of the antibody, a stable cell line expressing the antibody can be prepared, by transfecting cells (e.g. CHO cells) with the Ig expression vector containing both heavy and light chains of the chimeric antibody. Highly anti-eotaxin 2 (or any other CCR3-binding chemokine used for the production of the antibodies) antibody producing clones may be then selected and expanded based on antibody levels in the supernatant, as tested by any method known in the art, for example, a CCR3-binding chemokine-specific ELISA assay, as detailed herein below.

The term "humanized" antibodies traditionally refers to forms of non-human (for example, murine) antibodies that contain a human-derived immunoglobulin framework with minimal sequences derived from non-human immunoglobulin at the CDRs and optionally at additional relevant positions. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and activity.

As used herein the term "fully humanized" antibodies relates to antibodies designed to have only human sequences. The fully humanized antibodies of the present invention were prepared using the Composite Human Antibodies™ technology that minimizes immunogenicity of the antibodies in patients. In this humanization technology multiple sequence segments derived from variable (V) regions of unrelated human antibodies are used as acceptors for the complementarity determining regions (CDRs) of the starting antibodies. Through careful selection of human sequence segments and the application of in silico tools, CD4+ T cell epitopes are avoided so the risk of immunogenicity is reduced compared to standard humanized antibodies whilst antibody affinity and specificity is maintained. Such antibodies contain only human sequences and are thus defined as "fully humanized".

The term "human antibody" as used herein refers to an antibody that possesses an amino acid sequence corresponding to that of an antibody produced by a human and/or has been made using any of the techniques for making human antibodies known in the art. This definition specifically excludes a humanized antibody that comprises non-human antigen-binding residues.

Preparation of humanized and human antibodies is well known in the art. Antibodies may also be prepared using phage display. As known in the art, antibody phage display (APD) is based on genetic engineering of bacteriophages and repeated rounds of antigen-guided selection and phage propagation.

The APD process begins with antibody-library preparation, by preparation of quality RNA from the cell source chosen (e.g., peripheral blood mononuclear cells). This RNA is reverse-transcribed into cDNA, which is used for PCR of the VH and VL chains of the encoded antibodies. This step is followed by ligation of the variable heavy (VH) and variable light (VL) PCR products into a phage display vector, culminating in analysis of clones of mAbs.

In one embodiment, the present invention provides an isolated fully humanized poly-specific monoclonal antibody, which comprises a heavy chain variable region comprising the CDRH1 comprising the amino acid sequence of NSGMN denoted by SEQ ID NO. 5, or a variant thereof, the CDRH2 comprising the amino acid sequence WINTYNGE-PTYTDDFKG denoted by SEQ ID NO. 6, or a variant thereof, and the CDRH3 comprising the amino acid sequence HSYGSSYAMDN denoted by SEQ ID NO. 7 or a variant thereof, and a light chain variable region comprising: the CDRL1 comprising the amino acid sequence KASQS-VDYDGDSYMN denoted by SEQ ID NO. 8 or a variant thereof; the CDRL2 comprising the amino acid sequence VASNLKS denoted by SEQ ID NO. 9 or a variant thereof; and the CDRL3 comprising the amino acid sequence QQS-NEEPWT denoted by SEQ ID NO. 10 or a variant thereof.

In other words, the present invention providesa an isolated polyspecific antibody, or any antigen-binding fragment thereof, that binds to at least two CCR3-binding chemokines, wherein the antibody is a fully humanized antibody and comprises a heavy chain variable region comprising:
  a) the complementary determining region VH CDR1 comprising the amino acid sequence denoted by SEQ ID NO. 5 or a variant thereof;
  b) the complementary determining region VH CDR2 comprising the amino acid sequence denoted by SEQ ID NO. 6 or a variant thereof; and
  c) the complementary determining region VH CDR3 comprising the amino acid sequence denoted by SEQ ID NO. 7 or a variant thereof; and a light chain variable region comprising
  d) the complementary determining region VK CDR1 comprising the amino acid sequence denoted by SEQ ID NO. 8 or a variant thereof;
  e) the complementary determining region VK CDR2 comprising the amino acid sequence denoted by SEQ ID NO. 9 or a variant thereof; and
  f) the complementary determining region VK CDR3 comprising the amino acid sequence denoted by SEQ ID NO. 10 or a variant thereof.

In some embodiments the present invention provides an isolated polyspecific antibody, or any antigen-binding fragment thereof, that binds to at least two proinflammatory CCR3-binding chemokines for use in the treatment of fibrotic diseases, autoimmune inflammatory disorders, monocyte related disorders or allergic atopic disorders, wherein said antibody is a fully humanized antibody and comprises a heavy chain variable region comprising:
  a) the complementary determining region VH CDR1 comprising the amino acid sequence denoted by SEQ ID NO. 5 or a variant thereof;
  b) the complementary determining region VH CDR2 comprising the amino acid sequence denoted by SEQ ID NO. 6 or a variant thereof; and
  c) the complementary determining region VH CDR3 comprising the amino acid sequence denoted by SEQ ID NO. 7 or a variant thereof; and a light chain variable region comprising
  d) the complementary determining region VK CDR1 comprising the amino acid sequence denoted by SEQ ID NO. 8 or a variant thereof;
  e) the complementary determining region VK CDR2 comprising the amino acid sequence denoted by SEQ ID NO. 9 or a variant thereof; and
  f) the complementary determining region VK CDR3 comprising the amino acid sequence denoted by SEQ ID NO. 10 or a variant thereof.

The above CDR sequences CDRH1, CDRH2, CDRH3, CDRL1, CDRL2 and CDRL3 denoted by SEQ ID NO. 5, SEQ ID NO. 6, SEQ ID NO. 7, SEQ ID NO. 8, SEQ ID NO. 9 and SEQ ID NO. 10, respectively are also presented in the context of their respective heavy and light chains sequences: The amino acid sequence of the heavy chain of the isolated fully humanized poly-specific monoclonal antibody exemplified herein is denoted by SEQ ID NO: 3 and is of the amino acid sequence:

QIQLVQSGPELKKPGASVKVSCRASGYPFTNSGMNWVKQAPGKGLKWMGW

INTYNGEPTYTDDFKGRFAFSLETSASTAYLQINNLRNEDTATYFCASHS

YGSSYAMDNWGQGTSVTVSS

The amino acid sequence of the light chain of the isolated humanized poly-specific monoclonal antibody exemplified herein is denoted herein by SEQ ID NO: 4 and is of the amino acid sequence:

DIVLTQSPDSLAVSLGERATINCKASQSVDYDGDSYMNWYQQKPGQPPKL

LIYVASNLKSGIPARFSGSGSGTDFTLTISSLQPEDFATYYCQQSNEEPW

TFGGGTKVEIK

Therefore in further embodiments the isolated polyspecific antibody for use according to the invention is wherein said antibody is a fully humanized antibody comprising the heavy chain variable region denoted by SEQ ID NO:3 or a variant thereof and the light chain variable region denoted by SEQ ID NO: 4 or a variant thereof.

The present invention also encompasses variants of the heavy and light chain variable regions. The variants may include mutations in the complementarity determining regions of the heavy and light chains which do not alter the activity of the antibodies herein described, or in the framework region.

By the term "variant" it is meant sequences of amino acids or nucleotides different from the sequences specifically identified herein, in which one or more amino acid residues or nucleotides are deleted, substituted or added.

It should be appreciated that by the term "added", as used herein it is meant any addition of amino acid residues to the sequences described herein.

Variants encompass various amino acid substitutions. An amino acid "substitution" is the result of replacing one amino acid with another amino acid which has similar or different structural and/or chemical properties. Amino acid substitutions may be made on the basis of similarity in polarity, charge, solubility, hydrophobicity, hydrophilicity, and/or the amphipathic nature of the residues involved.

Typically, variants encompass conservative amino acid substitutions. Conservative substitution tables providing functionally similar amino acids are well known in the art. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Each of the following eight groups contains other exemplary amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M).

Conservative nucleic acid substitutions are nucleic acid substitutions resulting in conservative amino acid substitutions as defined above.

Variants in accordance with the invention also encompass non-polar to polar amino acid substitutions and vice-versa.

As used herein, the term "amino acid" or "amino acid residue" refers to naturally occurring and synthetic amino acids, as well as amino acid analogs and amino acid mimetics that function in a manner similar to the naturally occurring amino acids.

Variant sequences refer to amino acid or nucleic acids sequences that may be characterized by the percentage of the identity of their amino acid or nucleotide sequences with the amino acid or nucleotide sequences described herein (for example, the amino acid or nucleotide sequences of the heavy and light chains of the antibodies herein described).

In some embodiments, variant sequences as herein defined refer to nucleic acid sequences that encode the heavy and light chain variable regions, each having a sequence of nucleotides with at least 70% or 75% of sequence identity, around 80% or 85% of sequence identity, around 90%, 91%, 92%, 93%, 94%, 95%, 96%, 97%, 98% or 99% of sequence identity when compared to the sequences of the heavy and light chain variable regions described herein.

In some embodiments the isolated poly-specific humanized monoclonal antibody according to the invention is wherein its heavy chain variable region is encoded by a nucleic acid sequence which is at least 70% identical to the nucleic acid sequence of the heavy chain variable domain denoted by SEQ ID NO. 1 and wherein its light chain variable region is encoded by a nucleic acid sequence which is at least 70% identical to the nucleic acid sequence of the light chain variable domain denoted by SEQ ID NO. 2.

By the term "activity of the antibodies" it is meant the ability of the antibodies to bind to at least two CCR3-binding chemokines, and prerferably to inhibit a biological function mediated by such CCR3-binding chemokines.

Non-limiting examples of such biological functions are: inhibition of cell recruitment or chemotaxis (for example recruitment or chemotaxis of eosinophils or monocytes or fibroblasts), inhibition of the transition of fibroblasts to myoblasts, or reduction of cellular activation (for example as measured by Ca$^+$ update). The biological functions can be measured in vivo or in vitro using methods well known in the art. Several such assays are described in the Examples below.

Additional in vitro experiments for determining the binding of the antibody prepared according to the invention to its target protein include for example ELISA assays.

The present invention further encompasses any antigen-binding fragments of the isolated poly-specific monoclonal antibody of the invention. Such antigen-binding fragments may be for example Fab and F (ab')$_2$, which are capable of binding antigen. Such fragments may be produced by any method known in the art, for example by proteolytic cleavage, using enzymes such as papain (to produce Fab fragments) or pepsin (to produce F(ab')$_2$ fragments).

Thus in some embodiments the isolated poly-specific monoclonal antibody according to the invention is wherein said antibody is an antibody fragment selected from the group consisting of Fv, single chain Fv (scFv), heavy chain variable region capable of binding the antigen, light chain variable region capable of binding the antigen, Fab, F(ab)$_2$' and any combination thereof.

Interestingly, using epitope mapping, the inventors identified a specific epitope in Eotaxin 1, eotaxin 2, Rantes and MCP-3 to which the antibody of the invention (hCM101) binds.

The epitope to which the antibody of the invention (hCM101) binds in Eotaxin-2 comprises the amino acid sequence CMFFVSKRIP denoted by SEQ ID NO: 15, in Eotaxin-1 the epitope comprises the amino acid sequence CFNLANRKIPLQRL denoted by SEQ ID NO: 16, in rantes the epitope comprises the amino acid sequence AYIARPL-PRAHIKEYFY denoted by SEQ ID NO: 17 and in MCP3 the epitope comprises the amino acid sequence CCYRFINKKI denoted by SEQ ID NO: 18 (the "first part of the N-loop") and the amino acid sequence SYRRTTSSH denoted by SEQ ID NO: 19 (the "second part of the N-loop").

Figures 20A, 20B:
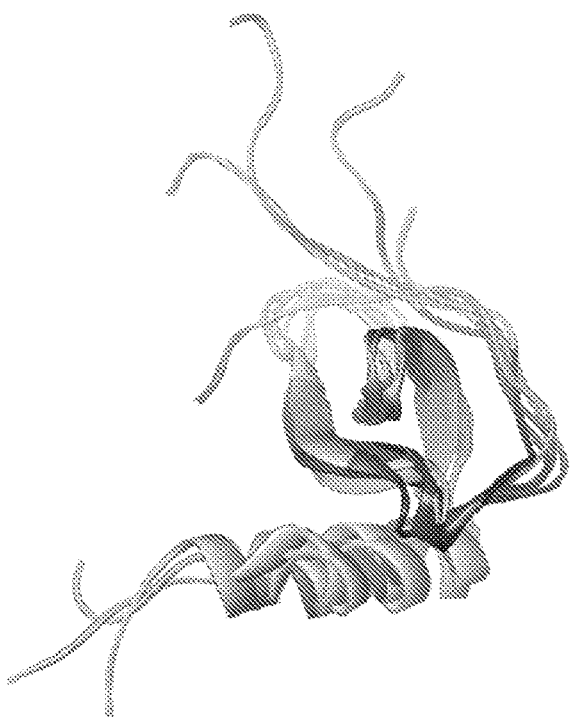
FIG. 20A is a graphic representation of the binding site of hCM101 in the N loop of Eotaxin 1, eotaxin 2, Rantes and MCP-3 (structures of the proteins are super imposed)
FIG. 20B shows amino acid sequence comparison of the assumed binding epitope in all four proteins.

As evident from the sequence alignment of these epitopes shown in FIG. 20B, the amino acid sequences of these epitopes are not identical. However, as schematically demonstrated in FIG. 21 A-D all of these epitopes are located at the same region within the CCR3-binding chemokine, namely at the N-loop region and evidently form a unique three dimensional structure which is recognized by hCM101. In other words, there is a common conformational epitope in the N loop of Eotaxin 1, eotaxin 2, Rantes and MCP-3 to which an antibody of the invention (hCM101) binds.

As used herein the term "conformational epitope" relates to an antigenic determinant, the part of an antigen that is recognized by the antibody, which is composed of continuous or discontinuous sections of the antigen's amino acid sequence. Conformational epitopes interact with the binding site of the antibody based on the 3-D surface features and shape, or tertiary structure, of the antigen. In certain instances, such epitopes may be identified partly by a linear sequence and by their relative position in the polypeptide's structure and by characteristic amino acids that are found within the identified epitope.

By the term "N-loop region" it is meant the N-loop and the turn towards the first beta strand located at the N terminus of CCR3-binding chemokines. For example, as shown in FIG. 21A (where the protein surface of Eotaxin-2 is shown) and in FIG. 21E (a ribbon diagram of Eotaxin-2), in the CCR3-binding chemokine Eotaxin-2, the N-loop region comprises the amino acid sequence CMFFVSKRIP denoted SEQ ID NO: 15.

Therefore in some embodiments the isolated antibody of the invention is wherein the conformational epitope comprises an amino acid sequences selected from the amino acid sequences denoted by SEQ ID NO: 15, SEQ ID NO: 16, SEQ ID NO: 17, SEQ ID NO: 18 or SEQ ID NO: 19.

Interestingly, bioinformatics analysis of the conformational epitope found in the N loop region of Eotaxin 1, eotaxin 2, Rantes and MCP-3 revealed several positively charged amino acid residues positioned either within the consecutive amino acid sequence portion of the epitope as defined above or in its vicinity. The epitopes are schematically shown in FIGS. 20 and 21. According to the bioinformatics analysis, the antibody binds a region within the CCR3-binding chemokine that includes a structure formed in the N loop region and involves amino acid residues at positions Lys-14 and Arg-15 (located within the epitope denoted by SEQ ID NO: 15) and Arg-20 in Eotaxin 2, positions Arg-16 and Lys-17 (located within the epitope denoted by SEQ ID NO: 16) and Arg-22 in Eotaxin 1, positions Arg-17 (located within the epitope denoted by SEQ ID NO: 17), His-23 and Arg-21 in Rantes, and positions Lys-18 and Lys-19 (located within the epitope denoted by SEQ ID NO: 18) and Arg-24 in MCP3. The identified amino acid positions within each of the chemokine sequence relates to the chemokine sequence without the N-terminal signal peptide, as shown in SEQ ID NOs: 11-14 corresponding respectively to the amino acid sequence (without the N-terminal signal peptide) of eotaxin 2, eotaxin 1, Tantes and MCP3.

By the term "position" it is meant the location within the amino acid sequence, where "position 1" indicates the first N-terminal amino acid residue after the signal peptide (namely the amino acid sequence of the mature polypeptide), "position 2" indicates the amino acid residue that is downstream to the N-terminal amino acid residue and so forth in the direction of N-terminal to C-terminal, as known in the art.

By the term "relatively high concentration" of positive amino acid residues it is meant at least three positive amino acid residues, e.g. three positive amino acid residues.

Therefore by another one of its aspects the present invention provides an isolated antibody that binds a conformational epitope in the N-loop region of a CCR3-binding chemokine, wherein said conformational epitope is characterized by a relatively high concentration of positive amino acid residues located between amino acid positions 14 and 24 in the amino acid sequence of said CCR3-binding chemokine.

In some specific embodiments the isolated antibody of the invention is wherein the conformational epitope comprises at least three positive amino acid residues between amino acid positions 14 and 24 in the amino acid sequence of said CCR3-binding chemokine.

In other specific embodiments the positive amino acid residues are selected from the group consisting of Arg, Lys and His.

In certain specific embodiments the isolated antibody of the invention binds to an epitope comprising amino acid residues at positions Lys-14, Arg-15 and Arg-20 in Eotaxin 2, positions Arg-16, Lys-17 and Arg-22 in Eotaxin 1, positions Arg-17, His-23 and Arg-21 in Rantes, and positions Lys-18, Lys-19 and Arg-24 in MCP3.

The common epitope as defined above can also serve for the screening and identification of additional antibodies having poly-specific binding capabilities to several CCR3-binding chemokines. Such antibodies would have high likelihood of being active in attenuating cell migration mediated by these chemokines.

Therefore, in another aspect, the present invention provides a method of screening and identifying antibodies capable of efficiently attenuating the migratory properties of at least one of CCR3, CCR1, CCR2 or CCR5 expressing cells.

In one embodiment said method comprising:
a. obtaining antibodies directed against a CCR3-binding chemokine; and
b. assessing the binding of said antibodies to a conformational epitope in the N-loop region of a CCR3-binding chemokine, wherein said conformational epitope is characterized by a relatively high concentration of positive amino acid residues located between amino acid positions 14 and 24 in the amino acid sequence of said CCR3-binding chemokine;
c. selecting antibodies which bind to said conformation epitope;
   wherein antibodies that bind specifically to said conformational epitope are capable of efficiently attenuating the migratory properties of CCR3, CCR1, CCR2 and CCR5 expressing cells.

In one embodiment, said conformational epitope comprises an amino acid sequence selected from the group consisting of the amino acid sequences denoted by SEQ ID NO: 15, SEQ ID NO: 16, SEQ ID NO: 17, SEQ ID NO: 18 and SEQ ID NO: 19.

In one specific embodiment the step of assessing the binding is performed by bringing the antibodies into contact with said conformational epitope, for example by incubating the antibodies with a fragment of the chemokine comprising the N-loop, or by incubating the antibodies with at least one of the amino acid sequences denoted by SEQ ID NO: 15, SEQ ID NO: 16, SEQ ID NO: 17, SEQ ID NO: 18 and SEQ ID NO: 19. The incubation may be performed by any method known in the art for assessing antigen-antibody binding, for example by ELISA or by using a chip containing multiple amino acid fragments. The incubation is performed in the presence of abinding buffer and antibody binding is assessed for example by a further incubation with a detectably labeled second antibody.

As used herein the term "screening and identifying" relates to the assessment of an antibody or a plurality of antibodies for their ability to bind to the epitope of the invention as defined above and selecting antibodies which bind to the epitope and thereby are expected to attenuate the activity of the CCR-binding chemokine upon binding to the chemokine.

In certain specific embodiments said conformational epitope comprises amino acid residues at the following positions: Lys-14, Arg-15 and Arg-20 in Eotaxin 2 (the amino acid sequence thereof is denoted by SEQ ID NO. 11), Arg-16, Lys-17 and Arg-22 in Eotaxin 1 (the amino acid sequence thereof is denoted by SEQ ID NO. 12), Arg-17, His-23 and Arg-21 in Rantes (the amino acid sequence thereof is denoted by SEQ ID NO. 13), and Lys-18, Lys-19 and Arg-24 in MCP3 (the amino acid sequence thereof is denoted by SEQ ID NO. 14).

The identified conformational epitope of the invention can also be used as an antigen for generating antibodies capable of efficiently attenuating the migratory properties of at least one of CCR3, CCR1, CCR2 or CCR5 expressing cells. Therefore, in another aspect, the present invention provides an isolated N-loop region of a CCR3-binding chemokine comprising a conformational epitope, wherein said conformational epitope is characterized by a relatively high concentration of positive amino acid residues located between amino acid positions 14 and 24 in the amino acid sequence of said CCR3-binding chemokine, for generating antibodies against said CCR3-binding chemokine. In specific embodiments, said isolated N-loop region comprises an amino acid sequence selected from the group consisting of the amino acid sequences denoted by SEQ ID NO: 15, SEQ ID NO: 16, SEQ ID NO: 17, SEQ ID NO: 18 and SEQ ID NO: 19.

In certain embodiments the present invention provides an isolated N-loop region of a CCR3-binding chemokine comprising a conformational epitope, wherein said conformational epitope is characterized by a relatively high concentration of positive amino acid residues located between amino acid positions 14 and 24 in the amino acid sequence of said CCR3-binding chemokine, for use in a method of generating antibodies against said CCR3-binding chemokine. In specific embodiments, said isolated N-loop region comprises an amino acid sequence selected from the group consisting of the amino acid sequences denoted by SEQ ID NO: 15, SEQ ID NO: 16, SEQ ID NO: 17, SEQ ID NO: 18 and SEQ ID NO: 19.

The present invention thus further provides a method for generating antibodies capable of efficiently attenuating the migratory properties of at least one of CCR3, CCR1, CCR2 or CCR5 expressing cells comprising obtaining the epitope of the invention and producing an antibody to said epitope using any method known in the art.

Methods for vaccinating animals and generating polyclonal and monoclonal antibodies are well known in the art.

In another one of its aspects the present invention provides an isolated nucleic acid molecule comprising a nucleotide sequence encoding an antibody or any antigen-binding fragment thereof according to the invention.

The term "nucleic acid" or "nucleic acid molecule" as herein defined refers to a polymer of nucleotides, which may be either single- or double-stranded, which is a polynucleotide such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides. The term DNA used herein also encompasses cDNA, i.e. complementary or copy DNA produced from an RNA template by the action of reverse transcriptase (RNA-dependent DNA polymerase).

The invention further provides an expression vector comprising the isolated nucleic acid molecule as herein defined.

"Expression vector" sometimes referred to as "expression vehicle" or "expression construct", as used herein, encompasses vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. The expression vector in accordance with the invention may be competent with expression in bacterial, yeast, or mammalian host cells, to name but few.

In yet another one of its aspects the present invention provides a host cell transfected with the isolated nucleic acid molecule according to the invention or with the expression vector according to the invention.

The term "host cells" as used herein refers to cells which are susceptible to the introduction of the isolated nucleic acid molecule according to the invention or with the expression vector according to the invention. Preferably, said cells are mammalian cells, for example CHO cells or NSO cells. Transfection of the isolated nucleic acid molecule or the expression vector according to the invention to the host cell may be performed by any method known in the art.

In yet another one of its aspects the present invention provides an immunoconjugate comprising the antibody or any antigen-binding fragment thereof according to the invention and an additional therapeutic agent, e.g. an anti-inflammatory agent.

The term "immunoconjugate" as herein defined refers to an antibody or any antigen-binding fragment thereof according to the invention that is conjugated (linked or joined) to an additional agent. Immunoconjugates may be prepared by any method known to a person skilled in the art, for example, by cross-linking the additional agent to the antibody according to the invention or by recombinant DNA methods.

The polyspecific antibody of the invention may be administered in combination with at least one additional therapeutic agent.

The term "additional therapeutic agent" used herein refers to any agent that may be used for treating fibrotic diseases, autoimmune inflammatory disorders, monocyte related disorders or allergic atopic disorders. In some embodiments the additional therapeutic agent is an additional anti-inflammatory agent or anti fibrotic agent. In accordance with certain embodiments said at least one additional therapeutic agent is selected from a group consisting of chemotherapeutics, cytokines, peptides, antibodies and antibiotics.

In certain embodiments, said additional therapeutic agent includes, but is not limited to methotrexate, a steroid, cyclosporine, NSAIDS (non-steroidal anti inflammatory drugs), steroids, interferon-beta, intravenous immune globulin (IVIG), pirfenidone, nintedanib, bosentan, or macicentan.

In certain embodiments the additional therapeutic agent is an additional antibody. The term "additional antibody" as herein defined refers to an antibody, which is not the antibody according to the invention, which may be used in combination with the antibody of the invention. Such antibody may be directed as a non-limiting example against TNFα, TNF receptor, IL6 receptor, or CD20.

The present invention further provides a pharmaceutical composition comprising as an active ingredient the isolated poly-specific antibody of the invention, or any antigen-binding fragment thereof or the immunoconjugate as herein defined and a pharmaceutically acceptable carrier, excipient or diluent.

The "pharmaceutical composition" of the invention generally comprises the antibody or any antigen-binding fragment thereof as herein defined and a buffering agent, an agent which adjusts the osmolarity of the composition and optionally, one or more pharmaceutically acceptable carriers, excipients and/or diluents as known in the art.

As used herein the term "pharmaceutically acceptable carrier, excipient or diluent" includes any and all solvents, dispersion media, coatings, antibacterial and antifungal agents and the like, as known in the art. The carrier can be solvent or dispersion medium containing, for example, water, ethanol, polyol (for example, glycerol, propylene glycol, and liquid polyethylene glycol, and the like), suitable mixtures thereof, and vegetable oils. Each carrier should be both pharmaceutically and physiologically acceptable in the sense of being compatible with the other ingredients and not injurious to the subject. Except as any conventional media or agent is incompatible with the active ingredient, its use in the therapeutic composition is contemplated.

In other embodiments the pharmaceutical composition according to the invention further comprises an additional therapeutic agent, e.g. an anti-inflammatory agent.

In specific embodiments the present invention relates to a pharmaceutical composition comprising an isolated poly-specific humanized antibody, or any antigen-binding fragment thereof, which binds to at least two proinflammatory CCR3-binding chemokines, wherein the antibody comprises a heavy chain variable region of the amino acid sequence denoted by SEQ ID NO. 3 or a variant thereof and a light chain variable region of the amino acid sequence denoted by SEQ ID NO. 4, or a variant thereof.

Further provided is a method of prophylaxis, treatment or amelioration of autoimmune inflammatory disorders, monocyte related disorders, allergic atopic disorders or fibrotic diseases comprising administering to a subject in need thereof a therapeutically effective amount of the isolated poly-specific antibody or any antigen-binding fragment thereof or the pharmaceutical composition according to the invention.

In some embodiments the invention provides a method of prophylaxis, treatment or amelioration of autoimmune inflammatory disorders, monocyte related disorders, allergic atopic disorders or fibrotic diseases comprising administering to a subject in need thereof a therapeutically effective amount of an isolated polyspecific humanized antibody, or any antigen-binding fragment thereof, which binds to at least two proinflammatory CCR3-binding chemokines, wherein the antibody comprises a heavy chain variable region of the amino acid sequence denoted by SEQ ID NO. 3 or a variant thereof and a light chain variable region of the amino acid sequence denoted by SEQ ID NO. 4, or a variant thereof.

The terms "subject" or "patient" are used interchangeably and refer to a subject that may benefit from the present invention such as a mammal (e.g. canine, feline, ovine, porcine, equine, bovine, or human). In one specific embodiment the patient is human.

By the term "prophylaxis" as herein defined it is meant to provide a "preventive treatment" or "prophylactic treatment", namely acting in a protective manner, to defend against or prevent an autoimmune inflammatory disorders, monocyte related disorders, allergic atopic disorders or fibrotic diseases, or an episode of such a disease.

It is to be understood that the terms "treat", "treating", "treatment" or forms thereof, as used herein, mean reducing, preventing, curing, reversing, ameliorating, attenuating, alleviating, minimizing, suppressing or halting the deleterious effects of a disease or a condition or delaying the onset of one or more clinical indications of a disease that is affected by proinflammatory CCR3-binding chemokines. Such diseases include autoimmune inflammatory disorders, monocyte related disorders, allergic atopic disorders or fibrotic diseases.

As used herein the term "treatment" refers to reducing, preventing, curing, reversing, attenuating, alleviating, minimizing suppressing or halting the deleterious effects of a disease or a condition that is mediated by eotaxin 2.

Administration according to the present invention may be performed by any of the following routes: oral administration, intravenous, intramuscular, intraperitoneal, intratechal or subcutaneous injection; intrarectal administration; intranasal administration, ocular administration or topical administration.

In specific embodiments administration according to the present invention may be performed intravenously. In other specific embodiments administration may be performed intraperitoneally. In other specific embodiments administration may be performed by inhalation.

The antibodies or antibody fragments as herein defined, any pharmaceutical compositions comprising the same or any conjugates comprising them may be administered to a subject prior to or post disease onset.

Thus in some embodiments the method of prophylaxis, treatment or amelioration of autoimmune inflammatory disorders, monocyte related disorders, allergic atopic disorders or fibrotic diseases according to the invention is where said isolated humanized poly-specific antibody or any antigen-binding fragment thereof according to the invention, or pharmaceutical composition according to the invention is administered to said subject prior to or after disease onset.

A "therapeutically effective amount" of the isolated monoclonal antibody or any antigen-binding fragment thereof according to the invention, or the pharmaceutical composition according to the invention for purposes herein defined is determined by such considerations as are known in the art in order to cure, arrest or at least alleviate or ameliorate the medical condition. For any preparation used in the methods of the invention, the dosage or the therapeutically effective amount can be estimated initially from in vitro cell culture assays or based on animal models such as the animal models detailed herein.

In some embodiments the therapeutically effective amount in accordance with the invention is in the range of 0.01 to 100 mg/kg.

In other embodiments the therapeutically effective amount in accordance with the invention is in the range of 0.01 to 40 mg/kg, 0.1 to 40 mg/kg or 1 to 10 mg/kg.

In other embodiments the isolated humanized poly-specific antibody or any antigen-binding fragment thereof according to the invention or pharmaceutical composition according to the invention is administered to the subject as a single dose or multiple doses.

The term "subject in need thereof" in the context of the present invention means warm-blooded animals, such as for example rats, mice, dogs, cats, guinea pigs, primates and humans suffering from autoimmune inflammatory disorders, monocyte related disorders, allergic atopic disorders or fibrotic diseases.

The present invention further provides the isolated humanized poly-specific antibody or any antigen-binding fragment thereof according to the invention or the pharmaceutical composition according to the invention for use in a method of prophylaxis, treatment or amelioration of autoimmune inflammatory disorders, monocyte related disorders, allergic atopic disorders or fibrotic diseases.

In specific embodiments the invention provides an isolated humanized poly-specific antibody, or any antigen-binding fragment thereof, which binds to at least two proinflammatory CCR3-binding chemokines, wherein the antibody comprises a heavy chain variable region of the amino acid sequence denoted by SEQ ID NO. 3 or a variant thereof and a light chain variable region of the amino acid sequence denoted by SEQ ID NO. 4, or a variant thereof for use in a method of prophylaxis, treatment or amelioration of autoimmune inflammatory disorders, monocyte related disorders, allergic atopic disorders or fibrotic diseases.

It is appreciated that the term "purified" or "isolated" refers to molecules, such as amino acid or nucleic acid sequences, peptides, polypeptides or antibodies that are removed from their natural environment, isolated or separated. An "isolated antibody" is therefore a purified antibody. As used herein, the term "purified" or "to purify" also refers to the removal of contaminants from a sample.

Materials and Methods

Specificity ELISA

The specificity of CM101 was assessed by ELISA. Plates were coated with the following antigens: eotaxin1, eotaxin2, monocyte chemoattractant protein-3 (CCL7), and RANTES (CCL5). All coated at 1 µg ml$^{-1}$ at 4° C. overnight. After washing (PBS+0.1% Tween 20), hCM101 (5 µg) was added to the plate for 1 h. After washing again, CM101 was detected with anti-human horseradish peroxidase conjugate (1 h incubation with 1:5000 dilution in PBS) and quantified using 3,3',5,5'-tetramethyl benzidine substrate (Sigma Chemical, Gillingham, UK). The reaction was stopped after 10 min with sulfuric acid (50 µl 2 M), and optical density was measured at 450 nM.

Immunohistochemistry:

Immunohistochemical staining for human Eotaxin 2/CCR3 was performed on 5-µm-thick frozen sections of skin/lung biopsies from scleroderma patients. After fixation with methanol and acetone, sections were blocked with nonimmune rabbit and goat sera, followed by incubation with CAS blocking reagent. Subsequently, the primary antibody (either the anti-Eotaxin-2 or anti CCR3 antibodies) was added for 1 hour at room temperature. After washing, biotinylated affinity-purified goat anti-mouse/rabbit antibodies (Jackson) were added. The slides were then incubated with 0.3% $H_2O_2$, followed by additional rinses and incubation with streptavidin-peroxidase conjugate (Jackson) for 30 minutes at room temperature. The slides were developed with 3-amino-9 ethylcarbazole substrate (Dako) for 15 minutes and counterstained with hematoxylin. H&E and Masson's Trichrome stains were used for analysis of lung inflammation and fibrosis changes in skin and lung sections.

Pulldown Assay

Pulldown was employed using dynabeads protocol (lifetechnology). Increasing concentrations of CM101 were incubated with magnetic beads (1 mg) for 1.5 hours in room temperature. Then, magnetic separation was performed followed by incubation overnight with human sera (from systemic sclerosis patient). Magnetic separation and elution of the chemokine from the beads was performed following by transfer into nitrocellulose membrane and exposure to commercial anti Eox2 antibody. The ability of hCM101 to bind eotaxin 1, Rantes and MCP-3 was also assessed using SDS gel electrophoresis.

Chemotaxis Assay

Aml 14.3D10, an Eosinophilic cell line that stably express CCR3 was washed once in PBS and resuspended at $10^7$ cells $ml^{-1}$ in assay buffer (RPMI 1640, 1% endotoxin-free BSA, 100 U $ml^{-1}$ penicillin, and 100 µg $ml^{-1}$ streptomycin). hCM101 at different concentrations ($10^{-7}$ M-$10^{-9}$M) was incubated with a combination of 5 nM human eotaxin-1 and eotaxin-2 or MCP-3 and RANTES (30 min, 37° C.) and placed into the lower chambers of 24-well Transwell plates with 5-µm pores (Costar); 100 µl of cells ($1 \times 10^6$ cells) were placed into the upper chamber of each Transwell plate, and the assay was incubated at 37° C. for 4 h (5% $CO_2$). Live cells migrating to the lower chamber were counted using a flow cytometer (FACSCalibur, BD Biosciences, Cowley, UK). Results are expressed as percent control (i.e., chemokine-induced) migration.

Experiments were also conducted with U937 monocytes cell line which expresses CCR1, CCR3 and CCR5. To assess the ability hCM101 to inhibit their migration, hCM101 was incubated with 5 nM mixture of MCP-3 and RANTES and placed into the lower chambers of 24-well Transwell plates with 5-µm pores (Costar). The assay was conducted as described above.

For CD14 positive cells, we used MACS separation magnetic Beads (Milteny) on Ficoll PBMCs isolated from scleroderma patients whole blood. Migration of CD14+ cells towards MCP3 and RANES was assessed as describe above. In addition CD14− cells migration was examined towards Eotaxin 1, 2 and RANTES treated with hCM101.

To assess the chemotaxis of adherent cells (fibroblasts-NHDF) in response to Eotaxin 2, we used a transwell with a 8-µm pore size (Costar) coated with fibronectin. After Eotaxin 2 was incubated with hCM101 for 30 minutes, NHDF cells (5×104 cells) were added to the upper chamber and incubated at 37° C. for 4 h. Then, non-migrating cells were removed from the insert membranes by cotton swabs. The membrane was fixed by 4% paraformaldehyde and migrated cells were then stained with commassie blue. The number of migrating cells was counted in three random fields using an inverted microscope and analyzed using image pro software.

Calcium Activation Assay:

Cells ($2 \times 10^6$ cells/ml) were incubated in PBS+/+(calcium magnesium++) with calcium sensor (Flou4-AM, invitrogen) to a final concentration of 4 µM for 30 min at 37°. Then, the cells were washed and incubated for another 30 min in 37° in 500 ul of PBS+/+. Cells were analyzed using flow cytometer for 30 sec (488 laser, filter 520), then stimulated with 100 ng/ml of eotaxin 2 (with or without preincubation with hCM101) and immediately proceeded the flow read.

Flow Cytometry Intracellular Staining:

Fibroblasts were incubated for 24 h with CM101 (10 or 5 µg/ml) and human sera. Then cells were trypsinized, fixated with 70% ethanol and incubated with anti a SMA Ab with the cells (Biolegend) for 0.5 h at room temperature cells were then washed and subjected to secondary Ab Cye3 Donkey α Rabbit IgG (1:300 in PBS) 0.5 h at room temperature. Cells were analyzed through flow cytometer.

In Vivo Scleroderma Model

Bleomycin (sigma) was dissolved in phosphate buffered saline (PBS) at 100 µg/ml.

Prevention Model:

Systemic sclerosis was induced via daily subcutaneous injections of 50 µg bleomycin to female C3H mice at age 6 weeks for 21 days. CM-101 (at doses of 5 µg, 10 µg, 20 µg or 50 µg), immunoglobulin G1 (IgG1) or PBS was injected every other day (starting on Day 1) in parallel with the initiation of bleomycin injections.

Treatment Model:

Female C3H mice at age 6 weeks were treated with subcutaneous injections of bleomycin (50 µg per day) for 20 days. Starting eight days following initiation of daily administration of bleomycin, mice were treated daily with 50 µg/day in 100 µl intraperitoneal injections of CM-101 or PBS and were sacrificed at day 21. Significantly, start of treatment with CM-101 occurred after onset of disease symptoms.

Mice were then killed, and full-thickness 6-mm punch biopsies were obtained from the injection site. Skin tissue harvest for paraffin and frozen blocks and for collagen assay. In addition, Blood was collected from the Orbital Sinus. Finally, the lungs were harvested for histology and broncho alveolar lavage (BAL) was conducted in order to examine leucocytes percentages (in PBS containing 0.1% BSA and 0.05 mM EDTA).

In Vivo IPF Model:

Prevention Model—

Male C57BL mice at age 7 weeks were treated with single dose of BLM (60 µg/mouse) via intratracheal injection under isoflurane anesthesia. BLM was dissolved in PBS. After injection the mice were placed in a vertical position and rotated for 1 min. CM-101 (at doses of 10 µg, 50 µg or 100 µg), immunoglobulin G1 (IgG1) or PBS were injected every other day (starting on Day 1) in parallel with the initiation of bleomycin injection.

Treatment Model:

Male C57BL mice at age 7 weeks will be treated with single dose of BLM (60 µg/mouse) via intratracheal injection under isoflurane anesthesia. BLM was dissolved in PBS. After injection the mice were placed in a vertical position and rotated for 1 min. Nine days following administration of bleomycin, mice were treated daily with 10 or 50 µg/day in 100 µl intraperitoneal injections of CM-101, IgG or PBS and were sacrificed at day 21. Significantly, start of treatment with CM-101 occurred after onset of disease symptoms. Nine days after bleomycin injections the PBS and bleomycin group were sacrificed for assessment of baseline fibrosis and inflammation. At day 21 the remained groups were sacrificed as well.

Mice were killed and lungs were harvested for histology and collagen measurement (sircol). Broncho alveolar lavage (BAL) was collected in order to examine leucocytes percentages (in PBS containing 0.1% BSA and 0.05 mM EDTA).

Measurement of Collagen Content

Soluble collagen was quantified using the Sircol soluble collagen assay (Biocolor, Belfast, UK). Skin samples were obtained from sclerodermic mice treated with either CM101 (5, 20 or 100 µg/ml), IgG or PBS. The samples were extracted into acid-pepsin solution. The samples were analyzed for collagen content according to the manufacturer's protocol. Briefly, 100 µl of sample was added to 1 ml of the colorimetric reagent (the dye SR in picric acid) and agitated for 30 min followed by centrifugation at 10,000 g for 10 min. The SR dye was released from the pellet with alkali reagent (1 N NaOH) and spectrophotometric readings were taken at 555 nm on a microplate reader.

Bal Assay:

The BAL assay was performed as previously described (Komai et al, 2010). The trachea was cannulated and the lung was washed 4 times with 0.5 ml calcium- and magnesium-free PBS containing 0.1% BSA and 0.05 mM EDTA-2Na. This procedure was repeated three times (total volume: 1.3 ml, recovery >85%). BAL from each animal was pooled in a plastic tube, cooled on ice, and centrifuged (150×g) at 4° C. for 10 min. Cell pellets were re-suspended in the same buffer (0.5 ml). Differential cell count was performing using flow cytometry.

Chemokines Levels

Eotaxin-1, Eotaxin-2 and Rantes levels were determined in the sera of scleroderma patients and healthy donors using the following Elisa kits: Quantikine human CCL11/Eotaxin, CCL24/Eotaxin-2 and CCL5/Rantes (R&D), according to the manufacturer's protocol.

Epitope Mapping

CHIP KMC was blocked with 0.05% Tween-20, 0.05% Triton X-100 in TBS buffer, pH 7.0, 4° C., overnight. The CHIP was washed with 1 mL 1 xTBS with 0.05% Tween-20 and 0.05% Triton X-100, pH7.0 and scanned at 635 nm and PMT 700. Then, to detect epitope binding of CM101, the CHIP was washed with 1 ml of binding buffer at 4° C. for 20 min and incubated with 1 Ctg/ml of hCM101 in binding buffer (pH 7.4) at 4° C. for 2 hours; Following the incubation, the CHIP was washed and incubated with 10 ng/ml anti-human IgG Alexa 647 conjugate in binding buffer (pH 7.4) at 4° C. for 1 hour. The CHIP was washed again and the canned at 635 nm and PMT 700.

Biacore Assay

The affinity constant of hCM101 or murine CM101 was evaluated using Biacore T100. This method uses Surface Plasmon Resonance (SPR) electrooptical phenomenon to measure the binding constants and on/off rates between binding partners. Eotaxin 2 was covalently immobilized on a surface of a CM-5 chip, and a solution of CM101 was passed over the surface. The changes in SPR angle were measured and enabled to determine the KD.

Episcreen Time Course T Cell Proliferation Assay

PBMCs from 20 healthy donors thawed, counted and viability assessed. For each donor, bulk cultures were established in which lml proliferation cell stock was added to the appropriate wells of a 24 well plate. Culture medium, 0.5 ml, and 0.5 ml of each diluted hCM101 were added to the PBMCs to give a final concentration of 50 ug/ml per sample. For each donor a reproducibility control (100 ug/ml KLH) and a culture medium only well were also included. Cultures were incubated for a total of 8 days at 37° C. with 5% CO2. On days 5, 6, 7 and 8, the cells in each well were pulsed with 0.75 uCi [3H]-Thymidine (Perkin Elmer, UK) in 100 ul AIM-V culture medium and incubated for 18 hours before harvesting using TomTec Mach III. Counts per minute (cpm) were determined by scintillation counting Meltilex (Perkin Elmer, UK).

Figure 1B:
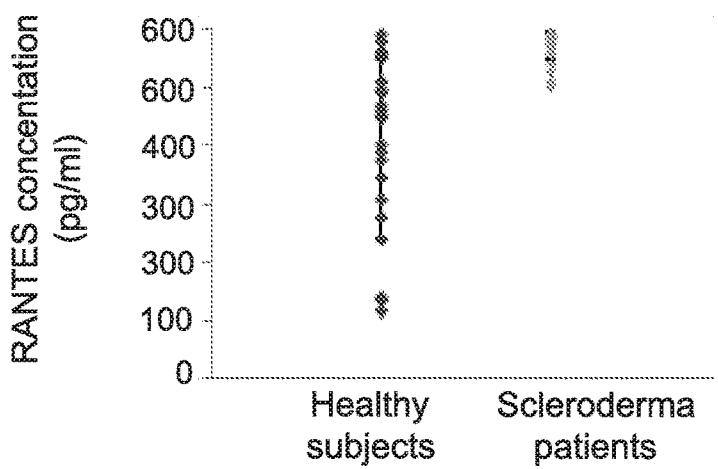
Figure 1C:
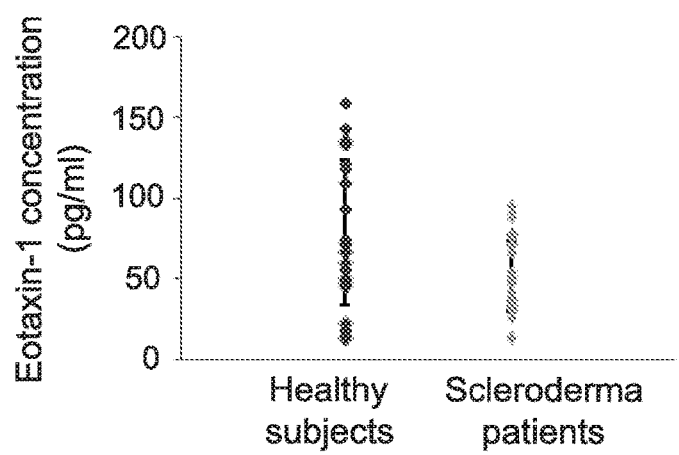

Example 1 Treatment with the Anti Eotaxin 2 mAb CM101 Reduces Scleroderma Features in a Mouse Model To examine the potential involvement of CCR3-binding chemokines in Scleroderma, the levels of Eotaxin 1, 2 and RANTES were assessed in the serum of scleroderma patients as compared to healthy subjects. The results indicated a significant increase in Eotaxin 2 and RANTES levels ($pv \leq 0.05$) as shown in FIGS. 1A and 1B, respectively. In addition, a significantly elevated expression of both Eotaxin 2 and its receptor, CCR3, was detected in skin biopsies taken from scleroderma patients (data not shown). It is thus possible that activation of the Eotaxin-2/CCR3 pathway may be operative in scleroderma.

The relevance of eotaxin 2 to scleroderma was further assessed using CM101. CM101 is a mouse monoclonal antibody directed against eotaxin 2 (WO2010/086854). The affinity constant (Kd) of CM-101 to murine eotaxin-2 was determined by Biacore and was found to be 7 nM. In order to evaluate the effect of treatment with CM101 on scleroderma, a bleomycin induced scleroderma murine model was used. Scleroderma was induced by a daily injection of 50 µg Bleomycin to C3H mice for 21 days. CM101 (10 µg, 20 µg or 50 µg), IgG or PBS were injected intraperitoneally every other day. Twenty one days after the onset of bleomycin injections, skin and BAL fluid samples were obtained from all groups. The mice were sacrificed for assessment of fibrosis and bronchoalveolar inflammation.

Figure 2A:
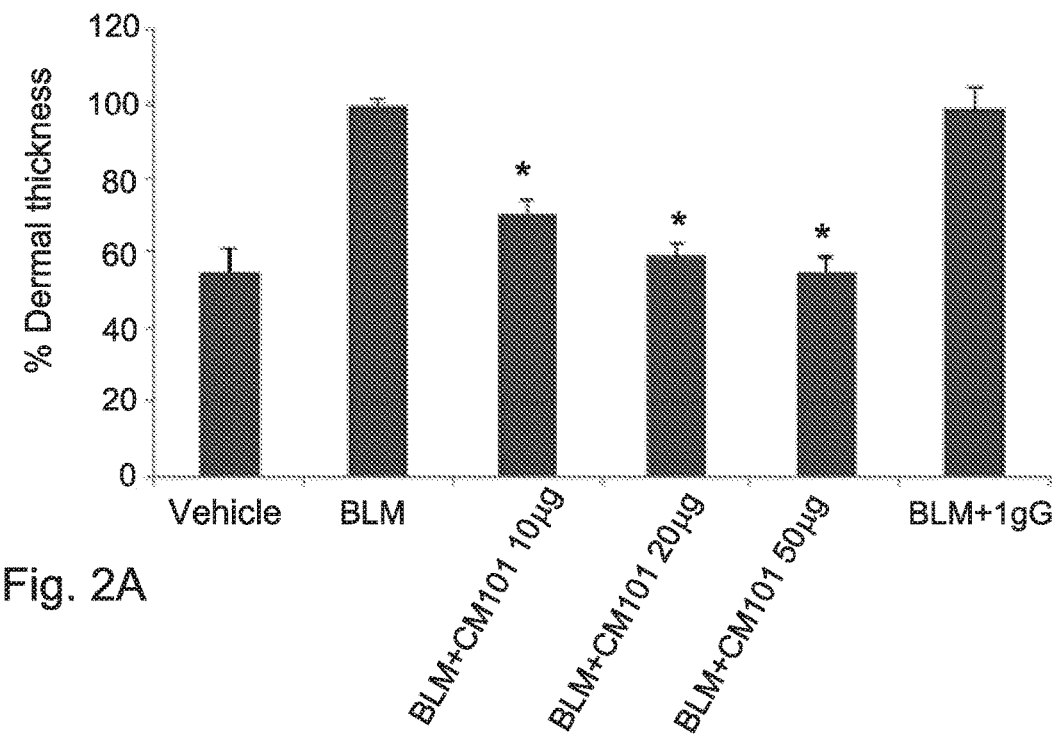
FIG. 2A-2B are graphs demonstrating the effect of CM101 treatment on different parameters in a prevention model in mice with bleomycin induced Scleroderma.
Figure 2B:
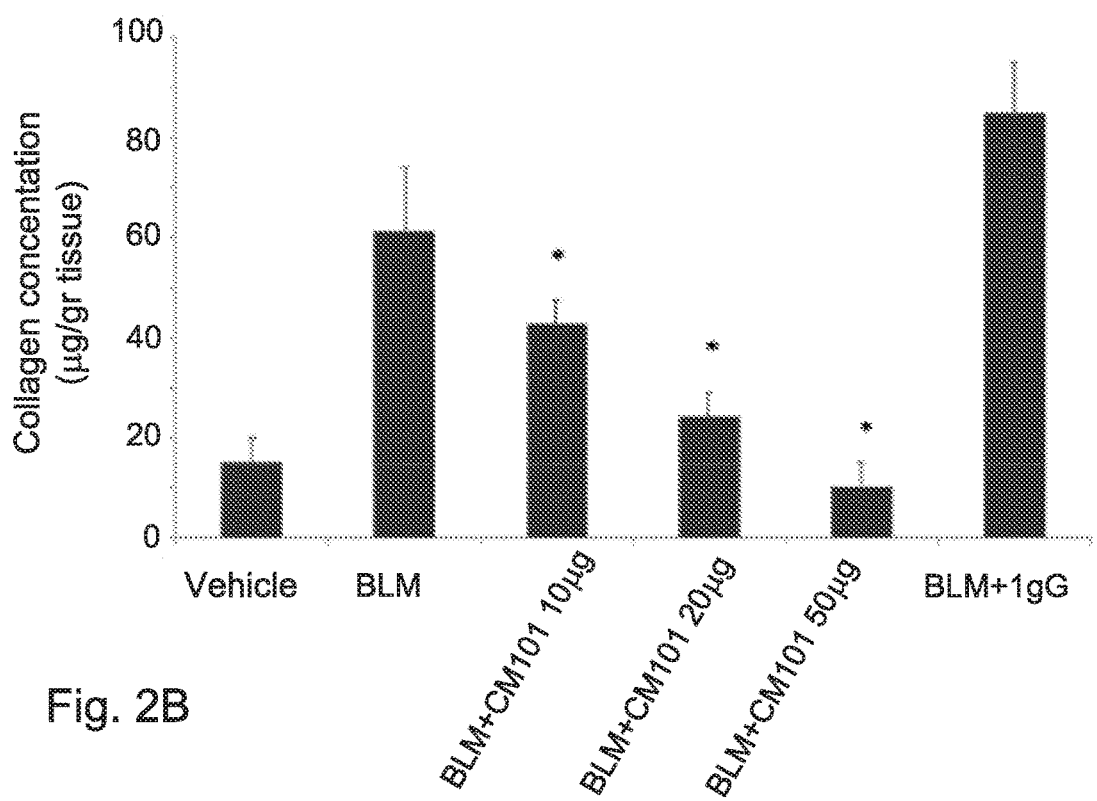
Figure 3A:
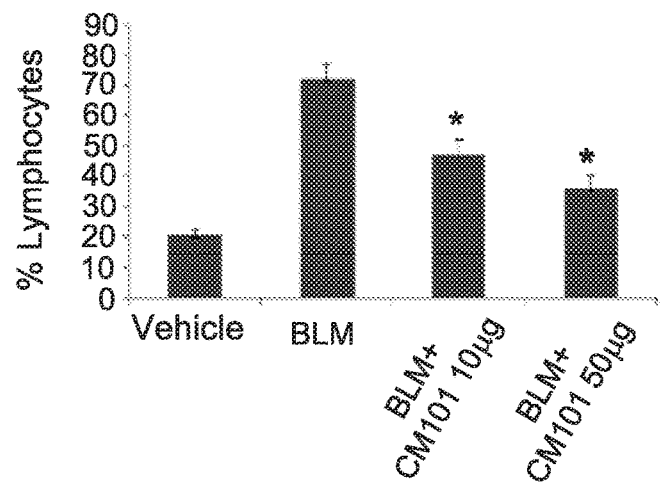
FIG. 3A-3B are graphs showing the effect of treatment with anti-eotaxin-2 monoclonal antibody (CM101 in 10 jag or 50 µg) on lymphocytes (FIG. 3A) and eosinophils (FIG. 3B) within the bronchoalveolar fluid of mice in a bleomycin-induced scleroderma model (prevention mode) (±standard error). * indicates p≤0.05. (Vehicle—no treatment (PBS); BLM-bleomycin)
Figure 3B:
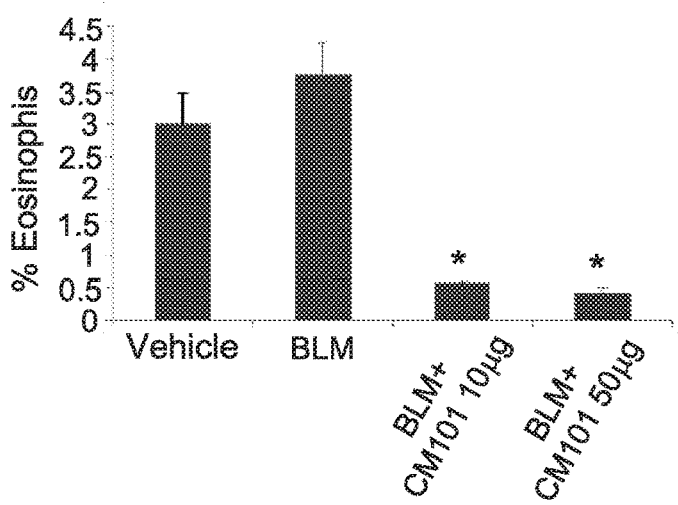

Significant decrease of severity of scleroderma related features was observed in mice treated with CM-101, compared to those treated with IgG1 or PBS. As shown in FIG. 2 and FIG. 3, CM-101 prevented the increase of all the tested parameters (dermal thickness, skin collagen content and leukocyte infiltration to the lung). In the dermal thickness test (FIG. 2A) statistically significant differences ($p<0.05$) were obtained for every dose of CM-101, as compared to treatment with PBS or with control IgG1. The preventive effect of CM-101 was also evident in the significant reduction of skin collagen concentration in a dose dependent manner (30%, 60%, and 84% reductions at the 10 µg, 20 µg, and 50 µg dose levels of CM-101, respectively, as shown in FIG. 2B). Determination of different leukocyte subsets in the murine bronchoalveolar lavage revealed a significant dose response reduction of lymphocyte and eosinophil percentages (FIGS. 3A and 3B, respectively).

In the treatment mode, eight days after bleomycin injections, skin and BAL fluid samples were obtained from the first (PBS) and second (bleomycin only) groups. 21 days after bleomycin injections onset, skin and BAL fluid samples were obtained from the third (bleomycin) and fourth (bleomycin+CM101) groups. The mice were sacrificed for assessment of fibrosis and bronchoalveolar inflammation.

Figure 4:
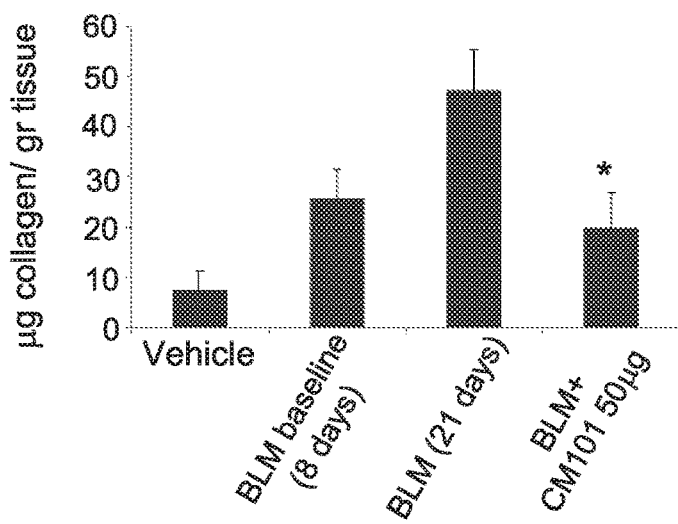
FIG. 4 is a graph showing the effect of treatment with anti-eotaxin-2 monoclonal antibody (CM101, 50 µg) and PBS (vehicle) on skin collagen concentration of mice in a treatment protocol (±standard error), *p≤0.05 (Vehicle—no treatment (PBS); BLM-bleomycin).

Skin collagen concentration was significantly reduced by 60% in the CM-101 treated group as compared to 21 days bleomycin treated group (FIG. 4)

Figure 5E:
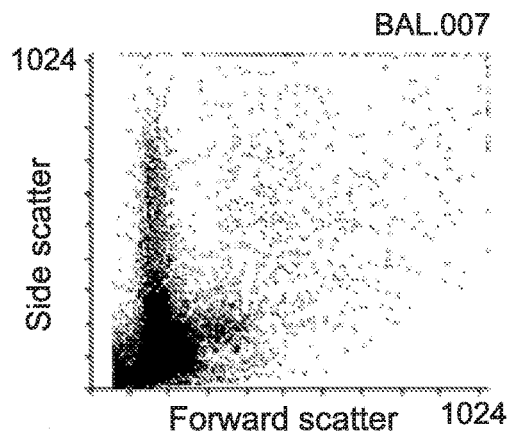
Figure 5F:
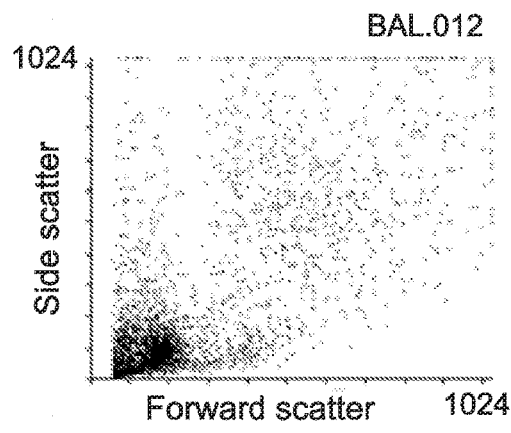

In addition BAL fluid was tested for leukocytes presence using flow cytometry analysis. Mononuclear cells and white blood cell infiltration was reduced significantly (55% and 30%, respectively) in CM-101 treated group as compared to bleomycin treated group as shown in FIGS. 5A and 5B. Representative flow cytometry figures are presented in FIG. 5C-5F.

Figure 6A:
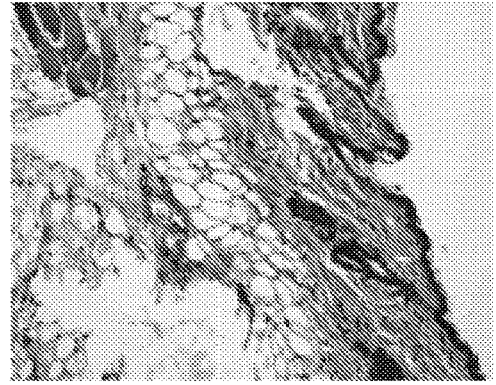
FIG. 6A-6D are photographs showing representative appearance of mice skin (hematoxylin eosin (H&E) staining).
Figure 6B:
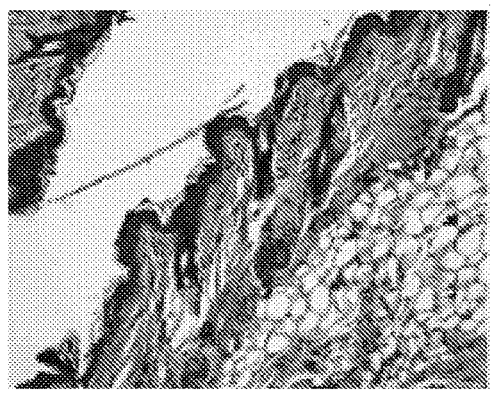
Figure 6C:
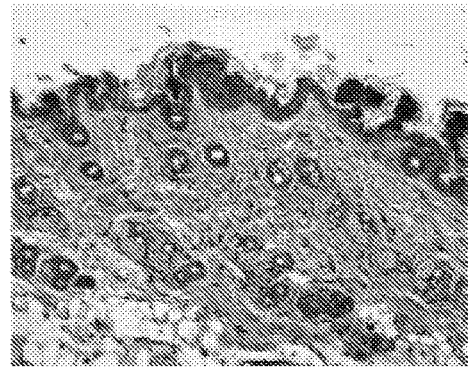
Figure 6D:
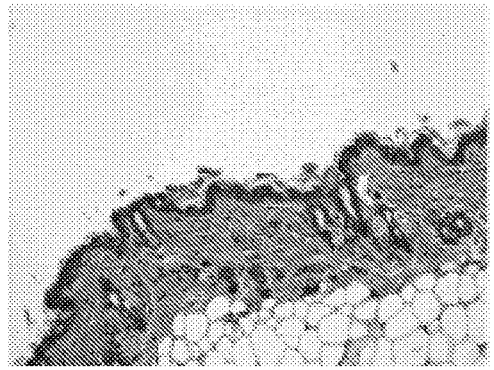
Figure 6E:
FIG. 6E-6H are photographs showing representative appearance of mice skin (Masson's Trichrome staining).
Figure 6F:
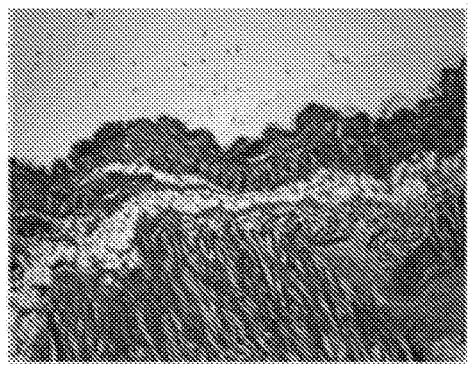
Figure 6G:
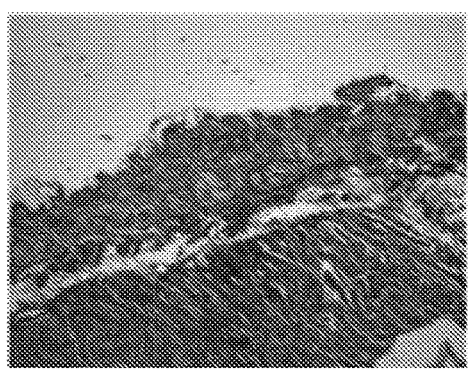
Figure 6H:
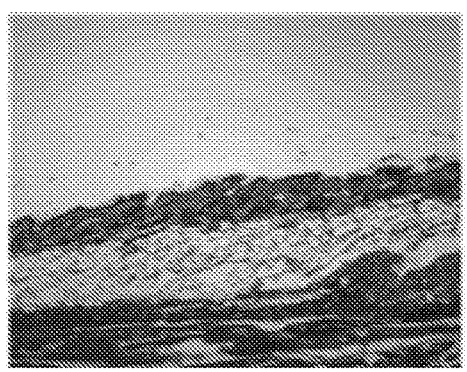

To evaluate dermal thickness, histopathology staining with hematoxilin eosin (H&E, FIG. 6A-D) and Masson's Trichrome (FIG. 6E-H) was performed on skin lesions. First, significant elevation was observed in dermal thickness following 21 days of bleomycin treatment as can be seen in FIGS. 6C and 6G. This elevation was not observed when mice were treated with CM-101 from day 8. In addition, H&E and Masson Trichrome staining revealed significant attenuation of inflammation and fibrosis in skin lesions of CM-101 treated group (FIGS. 6D and 6H) compared to BLM treated group.

Figure 7A:
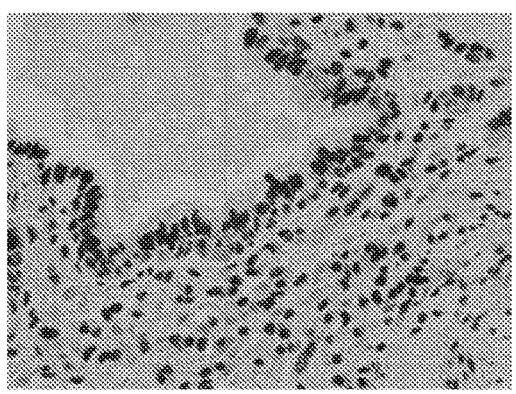
FIG. 7A-7B are photographs of lung lesions of IPF patients stained with hCM101.
Figure 7B:
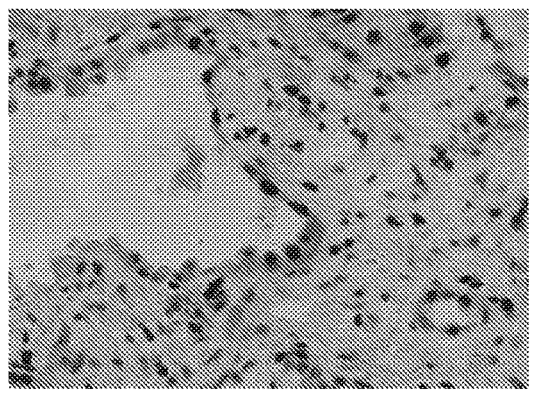

Example 2 Treatment with the Anti Eotaxin 2 mAb CM101 Reduces IPF in a Mouse Model To examine the potential involvement of eotaxin 2 in Idiopathic pulmonary fibrosis (IPF), the levels of eotaxin-2 were assessed in lung biopsies of IPF patients. A significantly elevated expression of eotaxin-2 was found in skin biopsies taken from IPF patients (shown in FIG. 7). These data support the idea that the eotaxin-2 pathway may be activated in IPF.

The common bleomycin induced lung fibrosis model was used to evaluate the efficacy of CM101. Bleomycin (60 µg per mouse) was injected intra tracheal to C57/B1 mice on day 1. In a prophylaxis protocol, CM101 or IgG were injected I.P from day 1 to day 14. 14 days following bleomycin injection, lung and BAL fluid samples were obtained from all groups. The mice were sacrificed for assessment of fibrosis and bronchoalveolar inflammation.

Figure 8:
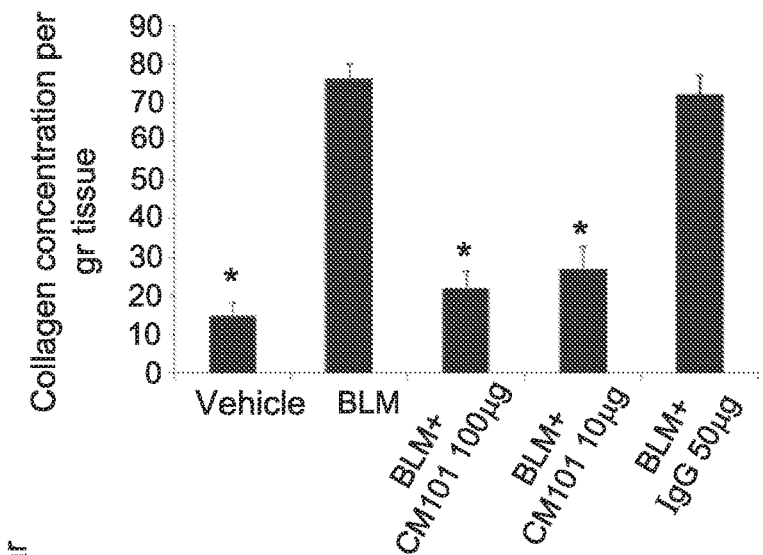
FIG. 8 is a graph showing the effect of treatment with anti-eotaxin-2 monoclonal antibody (CM101 in 10, 100 µg), IgG and PBS (vehicle) on the collagen concentration of mice in prevention mode of IPF (±standard error). *$pv \leq 0.05$. ***$pv \leq 0.01$. (BLM-bleomycin).
Figure 9:
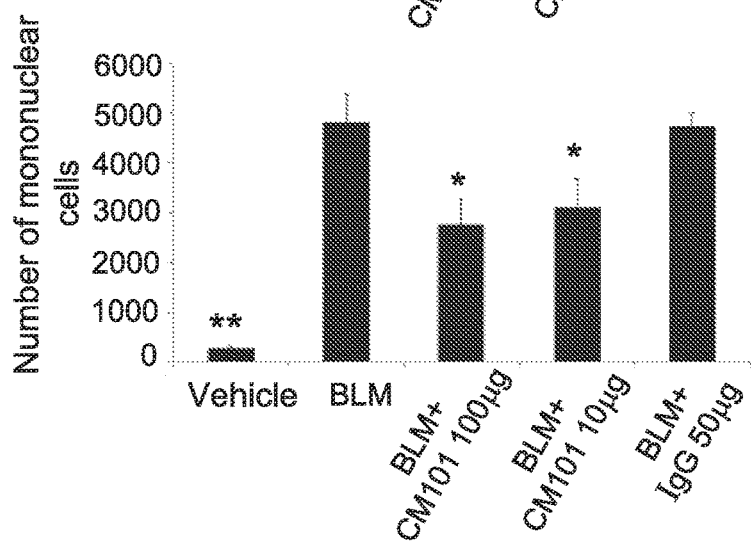
FIG. 9 is a graph showing the effect of treatment with anti-eotaxin-2 monoclonal antibody (CM101 in 10, 100 µg), IgG and PBS (vehicle) on mononuclear cells within the bronchoalveolar fluid of mice in prevention mode in IPF model (±standard error). *$pv \leq 0.05$. (BLM-bleomycin).
Figure 10:
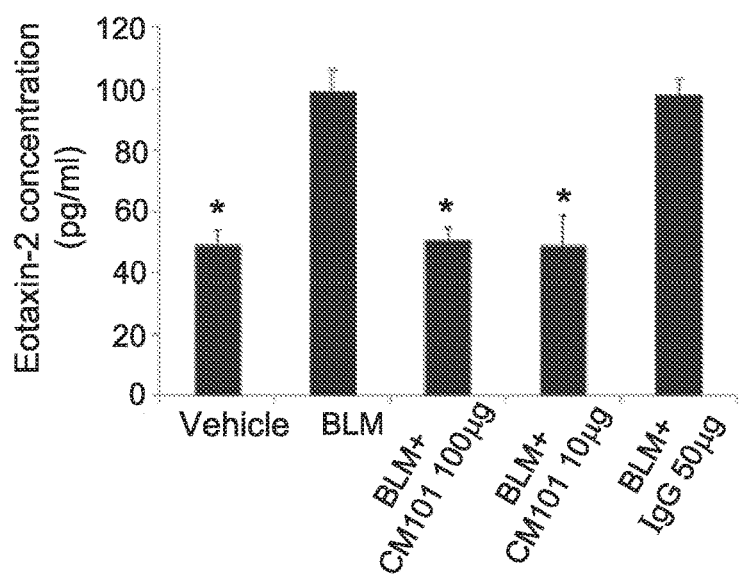
FIG. 10 is a graph showing the influence of CM101 (10, 100 µg) on the levels of Eotaxin 2 in the BAL fluid in prevention mode of IPF (±standard error). *$pv \leq 0.05$. (BLM-bleomycin, Vehicle-PBS).

Significant inhibition of IPF related features was observed in mice treated with CM-101, compared to those treated with immunoglobulin (IgG) or PBS. As shown in FIG. 8 and FIG. 9, inhibition by CM-101 was evident in all the tested parameters (collagen concentration and leukocytes infiltration to the lung). The inhibitory effect of CM-101 was evident in the significant reduction of collagen concentration in a dose dependent manner (60% and 70% reductions at the 10 µg and 100 µg dose levels of CM-101, respectively, as shown in FIG. 8). Measurement of mononuclear cells in the murine bronchoalveolar lavage (BAL) revealed a significant reduction (FIG. 9) following CM101 treatment. Measurement of Eotaxin 2 levels within BAL fluid revealed a reduction of Eotaxin2 within BAL fluid in the CM101 treated group (FIG. 10).

Figure 11:
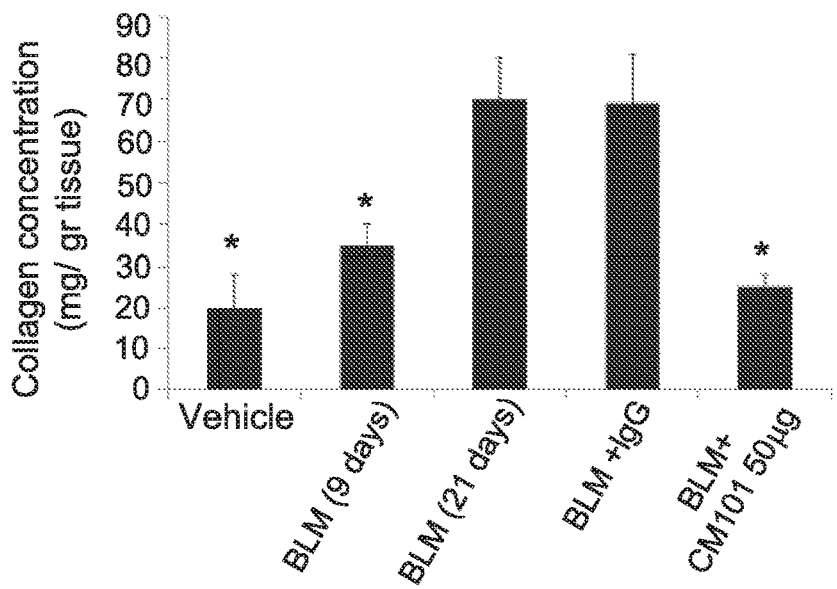
FIG. 11 is a graph showing the effect of treatment with anti-eotaxin-2 monoclonal antibody (CM101 in 50 µg), IgG and PBS (vehicle) on the lung collagen concentration of mice in treatment mode of IPF (±standard error). *$pv \leq 0.05$. **$pv \leq 0.01$. (BLM-bleomycin).

To evaluate CM101 efficacy after disease onset, a treatment protocol was performed where CM101 was administered daily only 10 days following BLM intra tracheal injection for the duration of 2 weeks. Lung collagen evaluation revealed a significant reduction (75%) following 50 µg CM101 daily treatments (FIG. 11).

Figure 12A:
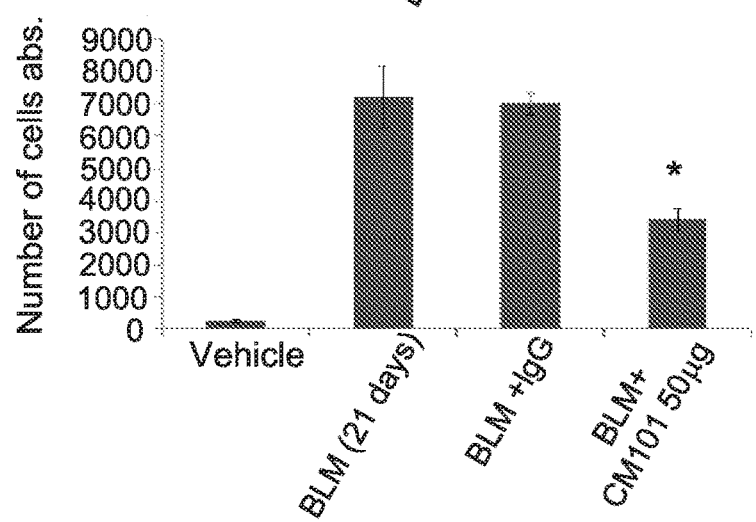
FIG. 12A-12B are graphs showing the effect of treatment with anti-eotaxin-2 monoclonal antibody (CM101 in 50 µg), IgG and PBS (vehicle) on mononuclear (FIG. 12A) and polymorphonuclear (FIG. 12B) cells within the bronchoalveolar fluid of mice in treatment mode in IPF model (±standard error). *$pv \leq 0.05$. (BLM-bleomycin).
Figure 12B:
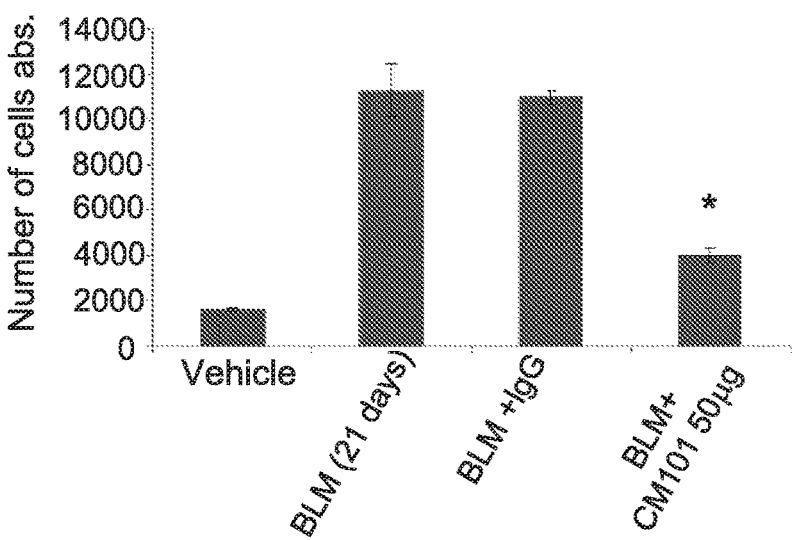

In addition BAL fluid was tested for leukocyte presence using flow cytometry analysis. Mononuclear cells, and polymorphonuclear cells infiltration were reduced significantly (55% and 65%, respectively) in CM-101 treated group as compared to bleomycin treated group as shown in FIGS. 12A and 12B. Pathological staining was performed on lung sections from each group and presented significant reduction in inflammation (H&E staining) and collagen deposition (Masson's Trichrome staining) as shown in FIG. 13.

A third in vivo model that was performed was a comparison between CM101 to the recently approved treatment for IPF: pirfenidone. Pirfenidone (5-methyl-1-phenylpyridin-2 [1H]-one) is a small molecule with anti fibrotic and some hydroxyl scavenger properties that has been approved by the FDA and EMA for the treatment of IPF as it was demonstrated to slow disease progression in patients with IPF.

IPF was induced as described in the previous experiment. Prior to BLM injection, mice were injected with either 100 µg CM101 I.P or fed daily with 100 mg/kg/day pirfenidone. Antibody injections were performed three times a week for two weeks while Pirfenidone oral gavage was performed daily for two weeks.

Figure 15A:
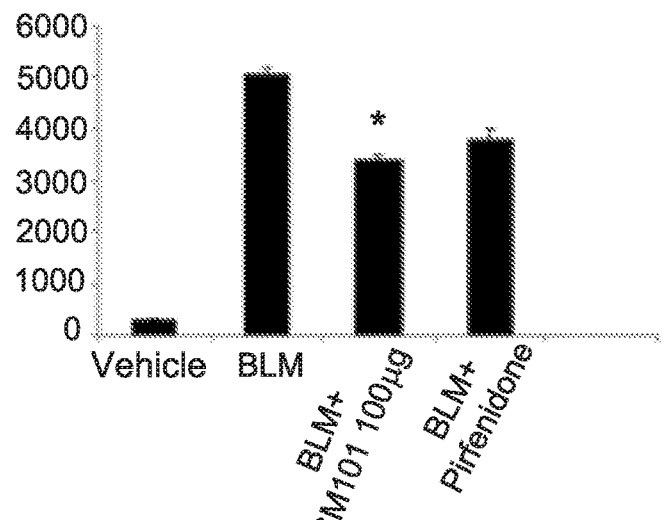
FIG. 15A-15C are graphs presenting the effect of CM101 (100 µg) compared to Pirfenidone (100 mg/kg/day) on mononuclear (FIG. 15A), polymorphonuclear (FIG. 15B) and white blood cells (FIG. 15C) within the bronchoalveolar fluid of mice in IPF model (±standard error). *$pv \leq 0.05$. **$pv \leq 0.01$. (BLM-bleomycin).
Figure 15B:
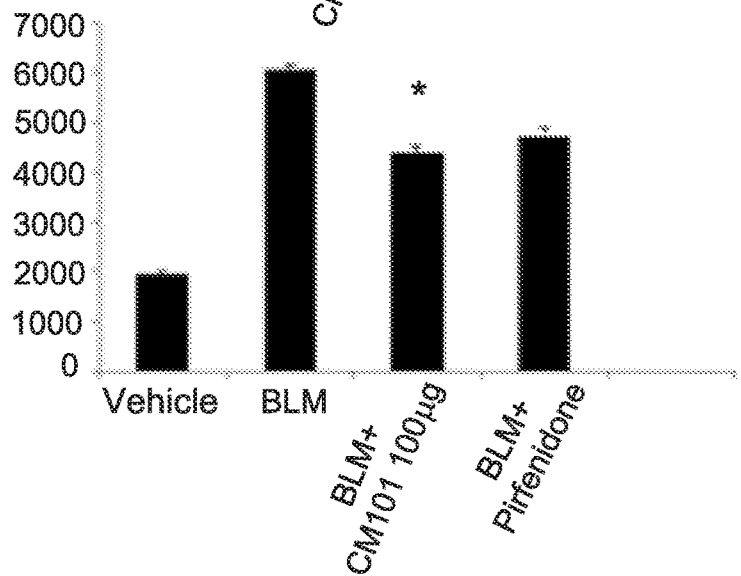
Figure 15C:
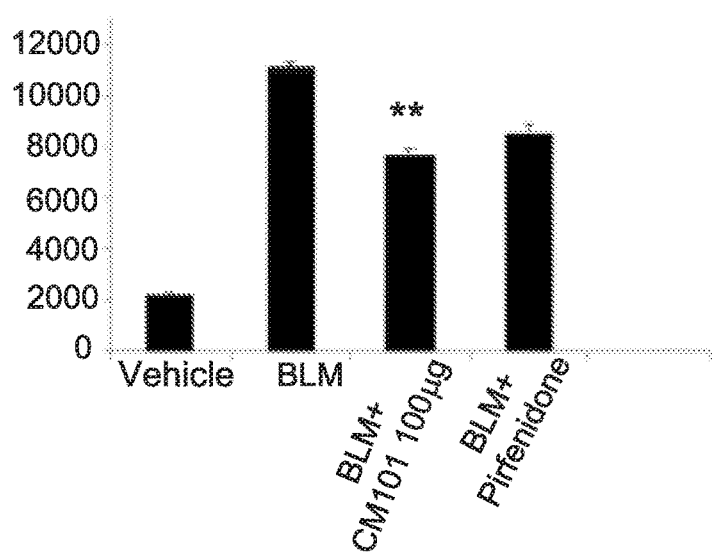

As shown in FIGS. 14 and 15, CM101 outperforms pirfenidone in all tested parameters. Lung collagen concentration was reduced more profoundly in CM101 treated mice as compared to pirfenidone treated mice. In addition, Measurement of mononuclear cells, white blood cells (WBC) and polymorphonuclear cells in the murine bronchoalveolar lavage (BAL) revealed a significant reduction in the CM101 treated group as opposed to the pirfenidone treated group (FIG. 15). Histological staining supports these results by showing less inflammation and fibrosis in lung lesion obtained from the CM101 treated group as compared with the pirfenidone treated group (data not shown).

Example 3 Producing the Humanized mAb hCM101

Variable (V) region genes from the murine antibody CM101 were cloned into Antitope vectors to generate a chimeric antibody comprising the murine V regions combined with the human IgG1 heavy chain constant region and κ light chain constant regions. The VH and Vκ sequences of the murine CM101 antibody were PCR amplified using primers that introduced flanking restriction enzyme sites for cloning into Antitope's IgG1 VH and Vκ chain expression vectors. The VH region was cloned using MluI and HindIII sites, and the Vκ region was cloned using BssHII and BamHI restriction sites. Both constructs were confirmed by DNA sequencing. Additionally, a series of four humanized VH regions for IgG1 and four humanized Vκ regions were designed and constructed using Composite Human Antibody™ technology (Antitope).

The chimeric antibody and the combinations of humanized V region genes (16 antibodies in total) were expressed in NSO cells, purified and tested for binding to human eotaxin-2 in a competition ELISA assay. The binding data were used to rank the humanized CM101 variants in comparison with the chimeric CM101 antibody. No significant differences in quality of the heavy and light chain bands were detected by SDS PAGE (data not shown).

Based upon the binding data, the humanized variant VH1/VK3 (hCM101) is selected as lead compound to be tested in the functional assays.

```
VH1/K3 sequence:
SEQ ID NO: 1:
CM101_VH1_DNA
CAGATCCAATTGGTGCAGTCTGGACCTGAGCTGAAGAAGCCTGGAGCCTC

AGTCAAGGTCTCCTGCAGGGCTTCTGGGTATCCCTTCACAAACTCTGGAA

TGAACTGGGTAAAGCAGGCTCCAGGAAAGGGTTTAAAGTGGATGGGCTGG

ATCAACACCTACAATGGAGAGCCAACATATACTGATGACTTCAAGGGACG

GTTTGCCTTCTCTTTGGAAACCTCTGCCAGCACTGCCTATTTGCAGATCA

ACAACCTCAGAAATGAGGACACGGCTACATATTTCTGTGCAAGTCATTCC
```

-continued

```
TACGGTAGTAGCTACGCTATGGACAACTGGGGTCAAGGAACCTCAGTCAC

CGTCTCCTCA

SEQ ID NO: 2:
CM101_VK3_DNA
GACATTGTGCTGACCCAATCTCCAGACTCTTTGGCTGTGTCTCTAGGGGA

GAGGGCCACCATCAACTGCAAGGCCAGCCAAAGTGTTGATTATGATGGTG

ATAGTTATATGAACTGGTACCAACAGAAACCAGGACAGCCACCCAAACTC

CTCATCTATGTTGCATCCAATCTAAAATCTGGCATCCCAGCCAGGTTTAG

TGGCAGTGGGTCTGGGACAGACTTCACCCTCACCATCAGCAGCCTGCAGC

CTGAGGATTTTGCAACCTATTACTGTCAGCAAAGTAATGAGGAACCGTGG

ACGTTCGGTGGAGGCACCAAGGTGGAAATCAAA

*CDR nucleotide sequences are bolded and
underlined.

SEQ ID NO: 3:
CM101_VH1_PROTEIN SEQUENCE
QIQLVQSGPELKKPGASVKVSCRASGYPFTNSGMNWVKQAPGKGLKWMGW
INTYNGEPTYTDDFKGRFAFSLETSASTAYLQINNLRNEDTATYFCASHS
YGSSYAMDNWGQGTSVTVSS

SEQ ID NO: 4:
>CMM01_VK3_PROTEIN SEQUENCE
DIVLTQSPDSLAVSLGERATINCKASQSVDYDGDSYMNWYQQKPGQPPKL
LIYVASNLKSGIPARFSGSGSGTDFTLTISSLQPEDFATYYCQQSNEEPW
TFGGGTKVEIK
```

The above nucleic acid sequence of VH variant 1 (heavy chain or VH) is defined herein as SEQ ID NO: 1.

The above nucleic acid sequence of Vκ variant 3 (light chain) is defined herein as SEQ ID NO: 2.

The above amino acid sequence of VH variant 1 (heavy chain or VH, 113 amino acids) is defined herein as SEQ ID NO: 3.

The above amino acid sequence of Vκ variant 3 (light chain, 107 amino acids) is defined herein as SEQ ID NO: 4.

VH variant 1 (the heavy chain) includes three complementarity determining regions (CDR):

VH CDR1 has the amino acid sequence NSGMN (SEQ ID NO: 5).

VH CDR2 has the amino acid sequence WINTYNGEPTYTDDFKG (SEQ ID NO: 6).

VH CDR3 has the amino acid sequence HSYGSSYAMDN (SEQ ID NO: 7).

Vκ variant 3 (the light chain) includes three complementarity determining regions (CDR):

Vκ CDR1 has the amino acid sequence KASQSVDYDGDSYMN (SEQ ID NO: 8).

Vκ CDR2 has the amino acid sequence VASNLKS (SEQ ID NO: 9).

Vκ CDR3 has the amino acid sequence QQSNEEPWT (SEQ ID NO: 10).

Example 4 Affinity and Binding Specificity of hCM101

Figure 16:
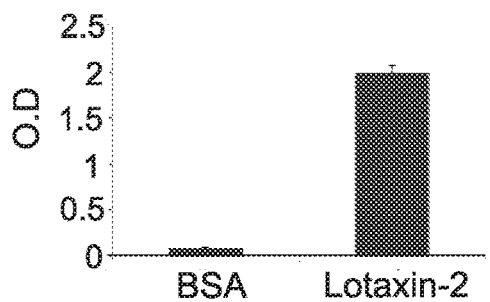
FIG. 16 is a graph showing binding of an anti eotaxin-2 mAb (hCM101) to eotaxin-2. The results are presented as optical density (OD) readings at 405 nm. (±standard error). $pv \leq 0.05$. (BSA—bovine serum albumin).

In order to examine the binding affinity of hCM101 to Eotaxin-2, but also to other related chemokines, several different methods were used: Elisa, Biacore, and epitope mapping by CHIP. Considerable binding of the antibody to Eotaxin 2 was demonstrated by Biacore (FIG. 16) and by Elisa revealing an affinity constant of $3 \times 10^{-9}$ M.

Figure 17:
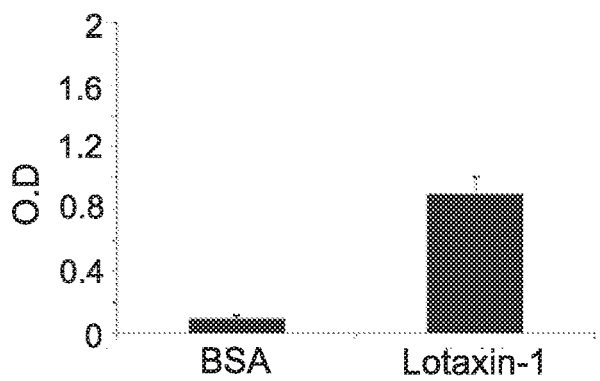
FIG. 17 is a graph showing binding of an anti eotaxin-2 mAb (hCM101) to eotaxin-1. The results are presented as optical density (OD) readings at 405 nm. (±standard error). $pv \leq 0.05$. (BSA—bovine serum albumin).
Figure 18:
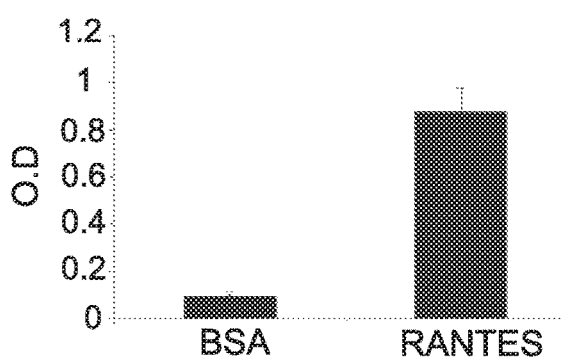
FIG. 18 is a graph showing binding of an anti eotaxin-2 mAb (hCM101) to RANTES. The results are presented as optical density (OD) readings at 405 nm. (±standard error). $pv \leq 0.05$. (BSA—bovine serum albumin).
Figure 19:
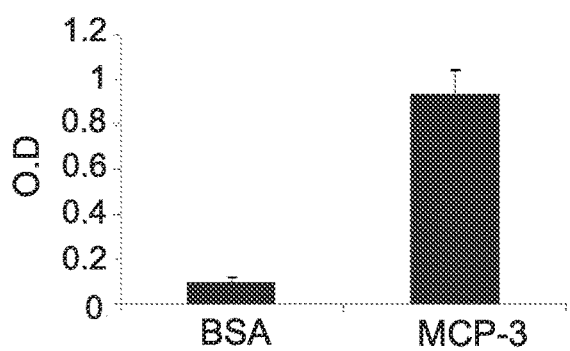
FIG. 19 is a graph showing binding of an anti eotaxin-2 mAb (hCM101) to MCP-3. The results are presented as optical density (OD) readings at 405 nm. (±standard error). $pv \leq 0.05$. (BSA—bovine serum albumin).

Surprisingly, hCM101 was found to bind with moderate affinity also to other related chemokines. As shown by Elisa hCM101 was found to bind to Eotaxin 1 (FIG. 17), RANTES (FIG. 18) and MCP3 (FIG. 19).

Epitope mapping analysis revealed a common feature between these four chemokines. It appears that Eotaxin 1, 2, Rantes and MCP-3 exhibit an epitope site that is located within the N loop (FIG. 20). This mutual binding site is characterized by high concentration of positive residues in approximately the same position (FIG. 21).

These results suggest that hCM101 is a poly-specific antibody that binds Eotaxin 2 with high affinity and other related chemokines as demonstrated by Elisa. Without wishing to be bound by theory, this feature may allow hCM101 to overcome chemokine redundancy and achieve efficacy.

In order to evaluate ex vivo the binding specificity of hCM101, a Pulldown of circulating Eotaxin 2 was performed from a representative serum of a systemic sclerosis patient with the fully humanized CM101 (hCM101) antibody. We found a dose dependant recognition of Eotaxin 2 by hCM101.

Figure 22A:
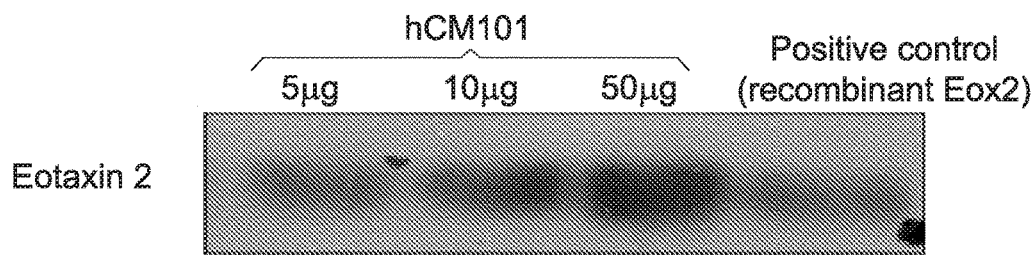
FIG. 22A-22B are representative gel (FIG. 22A) and densitometry of Eotaxin 2 levels pull-down (FIG. 22B) from systemic sclerosis sera by hCM101 (5, 10 and 50 µg). O.D.—optical density.
Figure 22B:
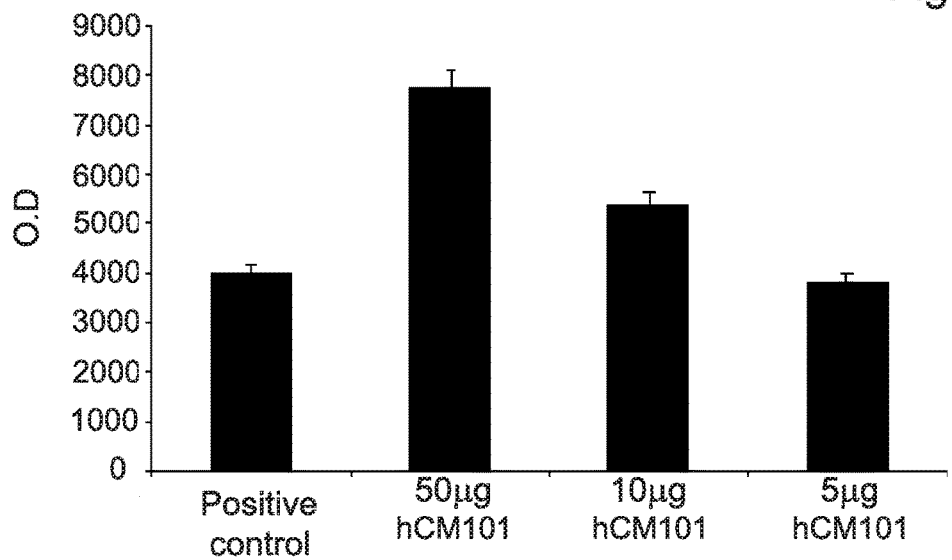
Figure 23:
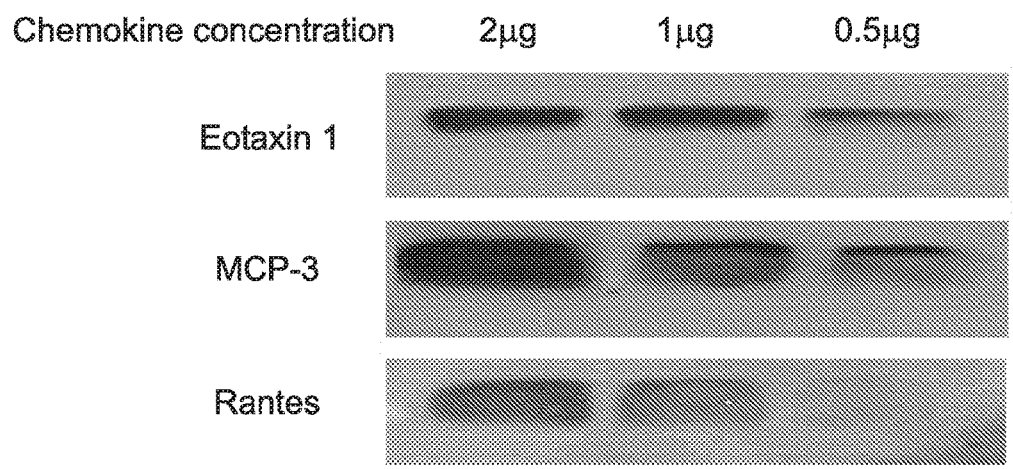
FIG. 23 demonstrates representative sodium dodecyl sulfate (SDS) gel analysis of Eotaxin 1, RANTES and MCP-3 (2, 1, 0.5 µg) detected by hCM101.

This result suggests a high specificity of hCM101 to eotaxin 2 within the sera (FIG. 22). In addition, using nitrocelluluse mebrane electrophoresis assay, increasing concentrations of eotaxin 1, Rantes and MCP-3 were exposed to hCM101. A specific dose increased binding of hCM101 to these chemokines was found (FIG. 23).

Example 5 Functional Assays Using hCM101

Eotaxin 1 and Eotaxin 2 are chemokines involved in the recruitment of Eosinophils into tissues through the binding and activation of CCR3.

Figure 24:
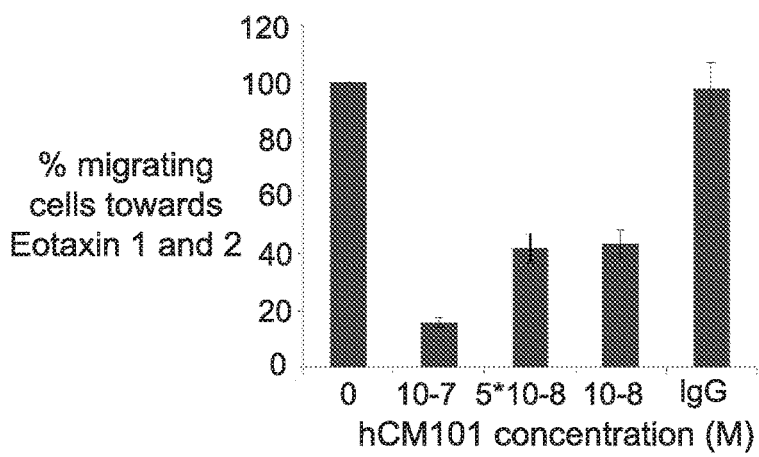
FIG. 24 is a graph showing the effect of hCM101 (100, 50 and 10 nM), IgG (50 nM) or PBS ("0") on eosinophils cell line migration towards eotaxin 1 and eotaxin 2 (±standard error). *$pv \leq 0.05$. **$pv \leq 0.01$.

For investigating potential anti-migratory function of hCM101, the antibody was incubated with these chemokines for 30 minutes in 37° C. and Eosinophil chemotaxis was examined. Results indicate a significant dose dependent inhibitory effect of hCM101 on Eosoniphil migration. 16% to 45% migration of the cells was observed in a $10^{-7}$ to $10^{-8}$ M antibody treatment, respectively (FIG. 24), pv≤0.05.

Figure 25:
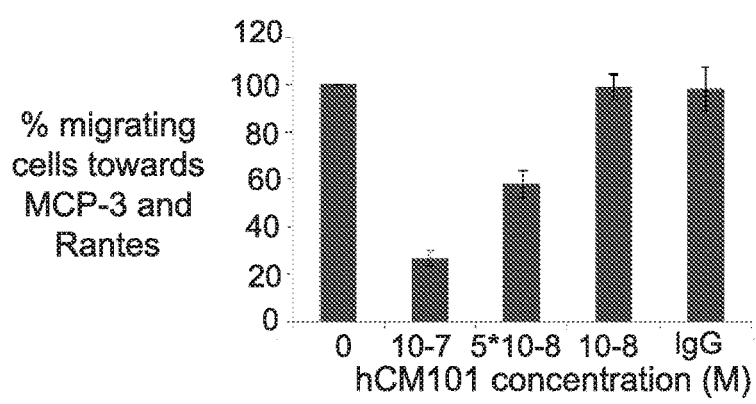
FIG. 25 is a graph showing the effect of hCM101 (100, 50 and 10 nM), IgG (50 nM) or PBS ("0") on monocytes cell line migration towards MCP-3 and RANTES (±standard error). *$pv \leq 0.05$.

Cells of the monocytes lineage are known to be primary targets for RANTES and MCP-3 by their binding to the CCR 1, 2, 3, 5 receptors. Thus, the effect of hCM101 on U937 monocyte cell line migration was examined by incubating the antibody with MCP-3 and RANTES. Monocyte chemotaxis was attenuated significantly demonstrating only 26% migration in 107M concentration of hCM101 (FIG. 25).

In addition in vitro monocyte chemotaxis assays were performed using isolated human monocytes and their relevant chemo attractants.

Figure 26A:
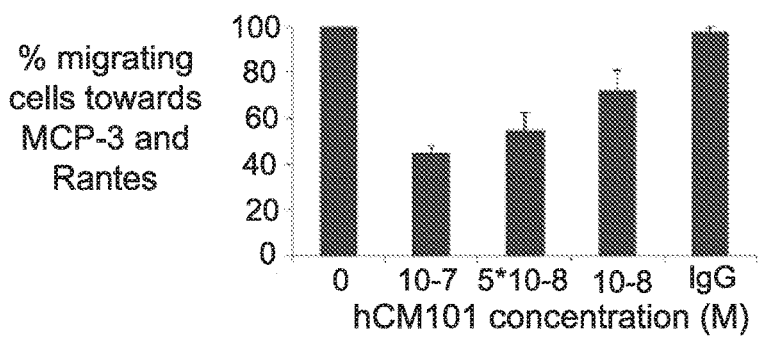
FIG. 26A is a graph showing the effect of hCM101 (100 and 10 nM), IgG (50 nM) or PBS ("0") on CD14+ cells (isolated from systemic sclerosis patient) migration towards MCP-3 and RANTES (±standard error). *$pv \leq 0.05$.

For this purpose, CD14+ monocytes sorted from PBMC obtained from scleroderma patients were allowed to migrate towards human MCP-3 and RANTES as attractants with or without different doses of hCM101. Treatment with hCM101 significantly attenuated monocyte chemotaxis by ~55% in the high dose (FIG. 26A).

Figure 26B:
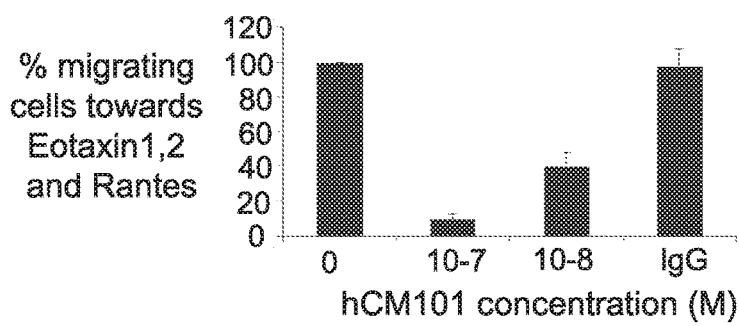
FIG. 26B is a graph showing the effect of hCM101 (100 and 10 nM), IgG (50 nM) or PBS ("0") on CD14− cells (isolated from systemic sclerosis patient) migration towards eotaxin 1,2 and RANTES (±standard error). *$pv \leq 0.05$, **$pv \leq 0.01$.

A similar experiment was performed on the migration of CD14 negative cells (mostly lymphocytes) towards Eotaxin 1, 2 and Rantes. hCM101 was found to significantly reduced by approximately 90% for the high dose of the antibody (FIG. 26B).

Figure 27A:
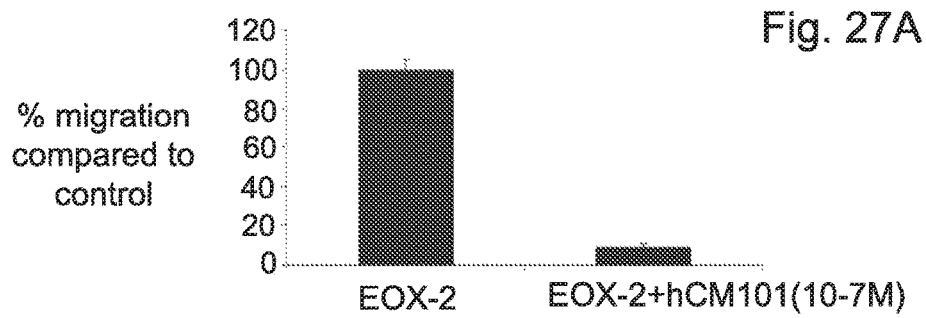
FIG. 27A is a graph showing the effect of hCM101 (100 nM) or PBS (EOX-2) on fibroblasts cell line migration towards eotaxin 2 (±standard error). **$pv \leq 0.01$.
Figures 27B, 27C, 27D:
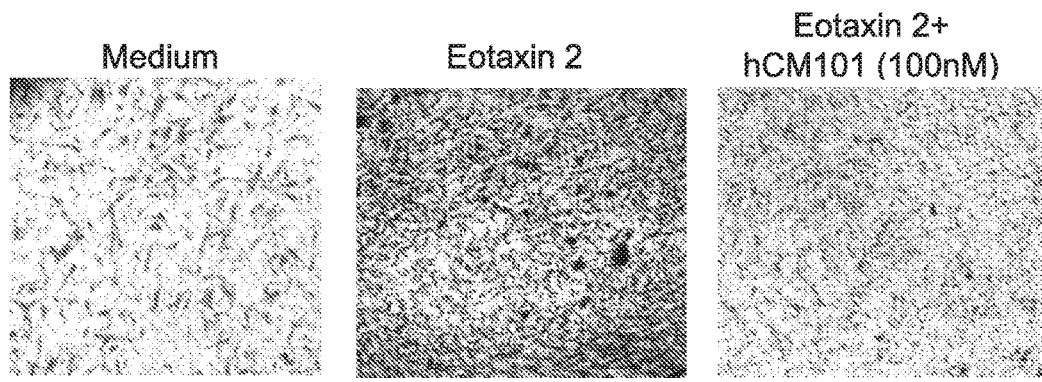
FIG. 27B-27D are representative pictures of a control (FIG. 27B), PBS-treated (FIG. 27C) and hCM101-treated (FIG. 27D) fibroblasts presented in FIG. 27A.
Figure 28A:
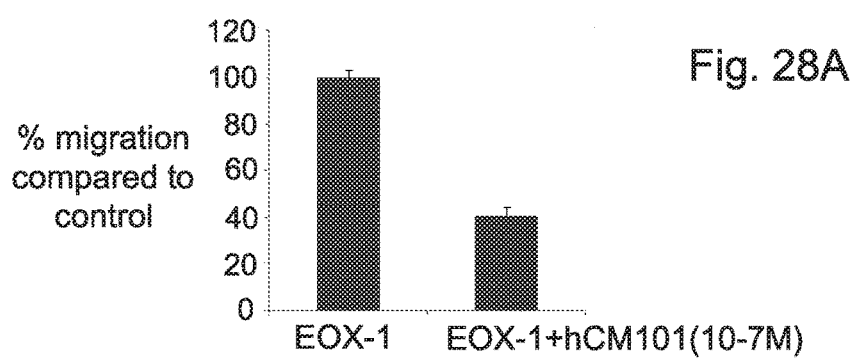
FIG. 28A is a graph showing the effect of hCM101 (100 nM) or PBS (EOX-1) on fibroblasts cell line migration towards eotaxin 1 (±standard error). *$pv \leq 0.05$.
Figures 28B, 28C, 28D:
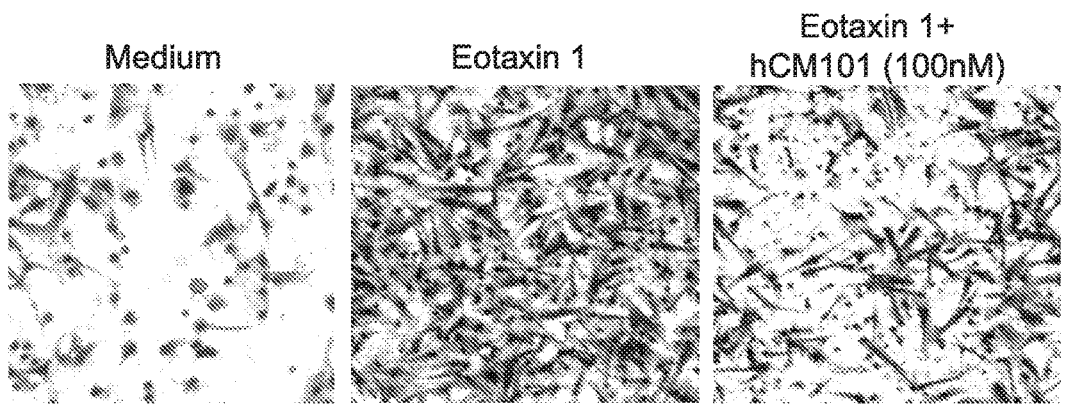
FIG. 28B-28D are representative pictures of a control (FIG. 28B), PBS-treated (FIG. 28C) and hCM101-treated (FIG. 28D) fibroblasts presented in FIG. 28A.
Figure 29A:
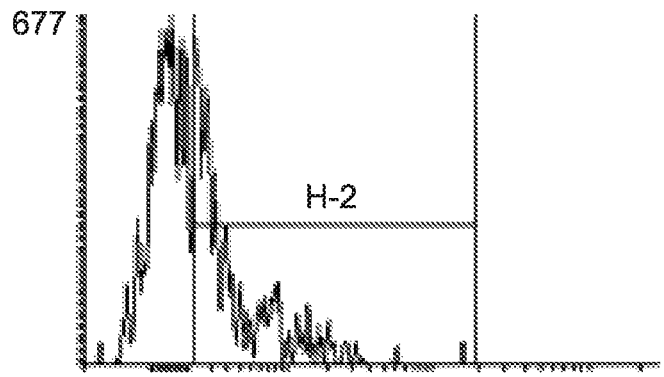
FIG. 29A-29C are representative FACS figures demonstrating the effect of hCM101 on intracellular expression of α-SMA as an indicator of myofibroblasts transition. $pv \leq 0.05$.
Figure 29B:
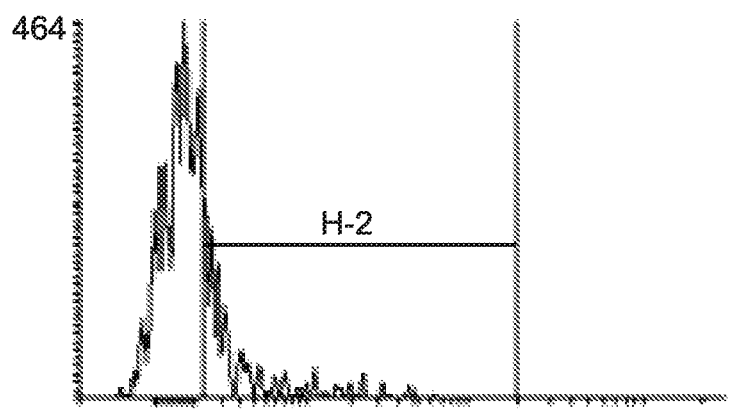
Figure 29C:
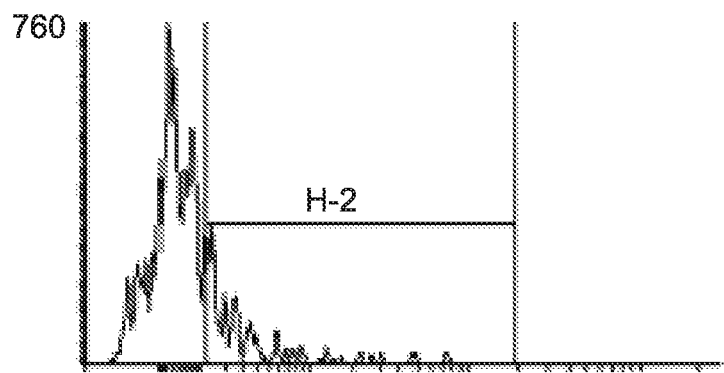

Scleroderma and IPF are fibrotic diseases that are well characterized by proliferation and migration of fibroblasts. To examine the effect of hCM101 on the migration of fibroblasts, a chemotaxis assay was performed towards Eotaxin 2 with or without hCM101. A significant reduction of migration was observed when hCM101 was added, as only 9% of the cells were adherent on the transwell compared to control (FIG. 27). Addressing the effect of hCM101 on Eotaxin-1, exhibited an inhibition of 60% of fibroblasts migration (FIG. 28).

The transition of fibroblasts to myofibroblasts is mirrored by elevated expression of smooth muscle actin.

The conversion of fibroblasts to myofibroblasts involves the expression of alpha-smooth muscle actin (α-SMA) and is a significant process in fibrosis. Their emergence can be induced by the presence of cytokines and chemokines in serum. In order to evaluate the influence of hCM-101 on the transition of fibroblasts to myofibroblasts, hCM-101 was incubated with sera from SSc patients, and then incubated these sera with human fibroblasts to measure their ability to induce α-SMA. α-SMA expression was evaluated by flow cytometry. As demonstrated in FIG. 30, the elevation of α-SMA was attenuated by 50% when the sera were incubated with CM-101 (10 μg/ml). These results suggest that CM-101 attenuates the conversion of fibroblasts to myofibroblasts stimulated by sera from systemic sclerosis (SSc) patients. This conversion is responsible for the excessive synthesis and remodelling of extracellular matrix (ECM) characterizing SSc.

The activation potency of chemokines is typically measured through calcium uptake into the cytosol. Incubation of CCR3 expressing cells with eotaxin-2 and different concentrations of hCM-101 demonstrated a significant reduction in calcium uptake (representing cellular activation), as shown in FIG. 30.

Example 6 hCM101 is not Immunogenic as Measured in an Episcreen Immunogenicity Test The lead fully humanized anti-Eotaxin-2 antibody (hCM101) was tested against a cohort of 20 healthy donors using EpiScreen™ time course T cell assay in order to determine the relative risk of immunogenicity. The samples were tested at a final concentration of 50 μg/ml hCM101 based on previous studies showing that this saturating concentration is sufficient to stimulate detectable antibody-specific T cell responses. In order to assess the immunogenic potential of each sample, the EpiScreen™ time course T cell assay was used with analysis of proliferation to measure T cell activation.

FIG. 31 illustrates the donor SI responses to hCM101 throughout the time course. The fully humanized anti-Eotaxin-2 antibody induced no positive responses using SI≥2.0, p<0.05 threshold in any of the donors in the proliferation assay.

Figure 32:
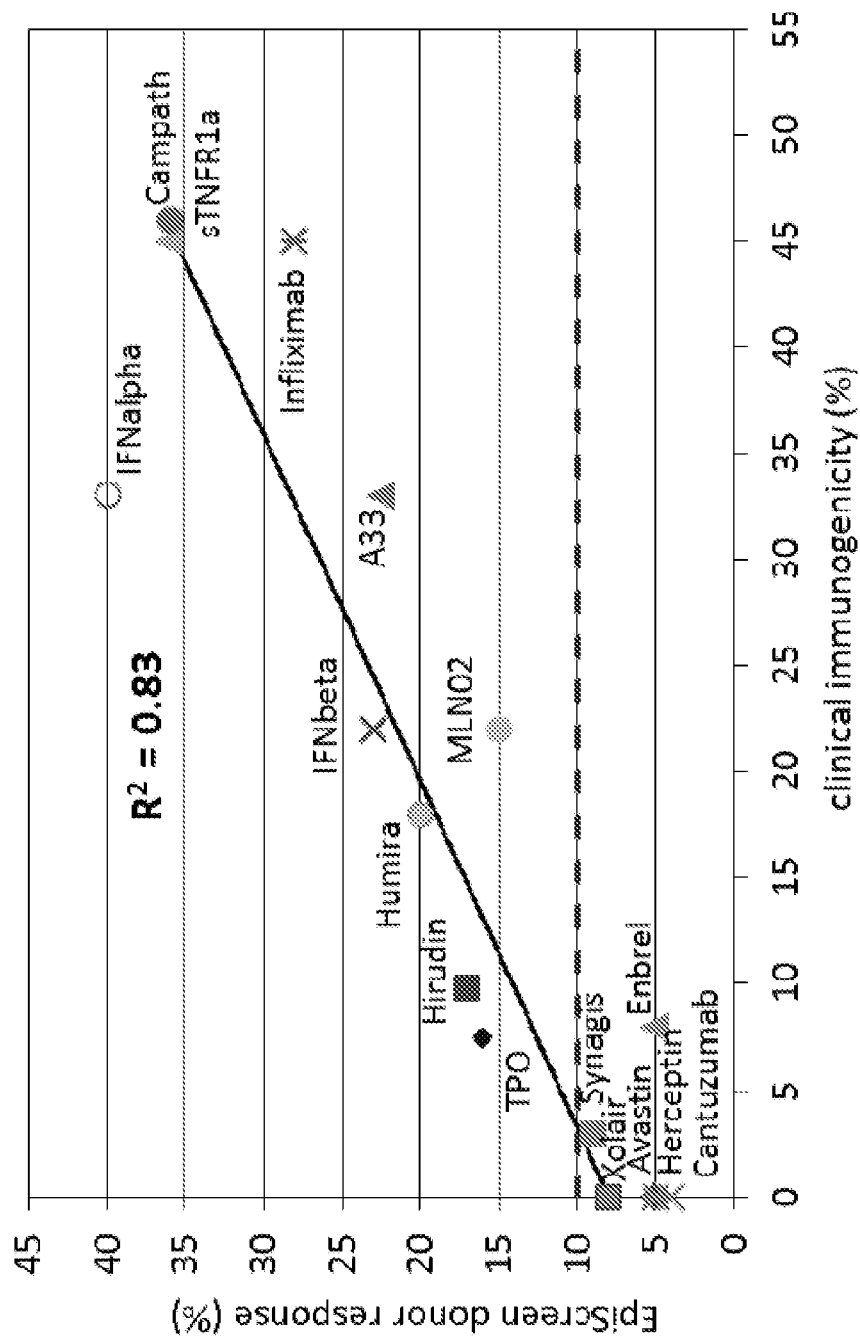
FIG. 32 is a graph showing the correlation between clinical immunogenicity (anti protein therapeutic antibody response) and T cell proliferation in Episcreen.

Previous EpiScreen™ time course T cell assays with a range of biologics (FIG. 32) have shown a clear correlation between the percentage of donor T cell responses in the EpiScreen™ assay and the level of immunogenicity (anti-protein therapeutic antibody responses) observed in the clinic. High frequency donor responses were observed in EpiScreen™ assays for immunogenic antibodies such as Campath, whereas relatively low frequency donor responses were observed for non-immunogenic antibodies such as Xolair and Herceptin. In general, protein therapeutics that induce <10% positive responses in the EpiScreen™ assay are associated with a low risk of immunogenicity in the clinic. The current study shows that, in comparison to other protein therapeutics tested in EpiScreen™ assays (FIG. 32), the fully humanized anti-Eotaxin-2 antibody hCM101 falls into the same range as Xolair, Herceptin and Avastin, and would be considered as having a low risk of immunogenicity.

REFERENCES

1. Goodnow C C et al, Cellular and genetic mechanisms of self tolerance and autoimmunity. Nature 2005; 2; 435(7042):590-7.
2. Jose P J, Griffiths-Johnson D A, Collins P D et al., Eotaxin: a potent eosinophil chemoattractant cytokine detected in a guinea pig model of allergic airways inflammation, J Exp Med 1994; 179: 881-887.
3. Kitaura M, Nakajima T, Imai T, et al., Molecular cloning of human eotaxin, an eosinophil-selective CC chemokine, and identification of a specific eosinophil eotaxin receptor, CC chemokine receptor 3, J Biol Chem 1996; 271: 7725-7730.
4. Ponath P D, Qin S, Ringler D J, et al., Cloning of the human eosinophil chemoattractant, eotaxin. Expression, receptor binding, and functional properties suggest a mechanism for the selective recruitment of eosinophils. J Clin Invest 1996; 97: 604-612.
5. Bocchino V, Bertorelli G, Bertrand C P, et al., Eotaxin and CCR3 are up-regulated in exacerbations of chronic bronchitis, Allergy 2002; 57: 17-22.
6. Fulkerson P C et al, Targeting eosinophils in allergy, inflammation and beyond; Nat Rev Drug Discov. 2013 February; 12(2):117-29.
7. Amerio. p et al, Eotaxins and CCR3 receptor in inflammatory and allergic skin diseases: therapeutical implications. Curr Drug Targets Inflamm Allergy. 2003; 2(1):81-94.
8. Pope S M, et al, The eotaxin chemokines and CCR3 are fundamental regulators of allergen-induced pulmonary eosinophilia. J Immunol. 2005 15; 175(8):5341-50.
9. Ablin, JN. Protective effect of eotaxin-2 inhibition in adjuvant-induced arthritis. Clin Exp Immunol. 2010; 161 (2):276-83.
10. Mausner et al, Eotaxin-2 blockade ameliorates experimental autoimmune encephalomyelitis World J Immunol 2013 27; 3(1): 7-14
11. Gu Y S et al, The immunobiology of systemic sclerosis. Semin Arthritis Rheum. 2008 October; 38(2): 132-60.
12. Bhattacharyya S, et al. Understanding fibrosis in systemic sclerosis: shifting paradigms, emerging opportunities Nat Rev Rheumatol. 2011 Oct. 25; 8(1):42-54.
13. Dulkys Y, et al. Detection of mRNA for eotaxin-2 and eotaxin-3 in human dermal fibroblasts and their distinct activation profile on human eosinophils. J Invest Dermatol. 2001.
14. Huaux et al. Role of Eotaxin-1 (CCL11) and CC chemokine receptor 3 (CCR3) in bleomycin-induced lung injury and fibrosis. Am J Pathol. 2005; 167(6):1485-96.
15. Martin Kohan, Et al. Eotaxin-2/CCL24 and eotaxin-3iCCL26 exert differential profibrogenic effects on humanlung fibroblasts.
16. Baggiolini, M. et al Eotaxin: a VIC (very important chemokine) of allergic inflammation? 1996 *J. Clin. Invest.* 97:587.
17. Baggiolini, M., B. et al., Human chemokines: an update. 1997, Annu. Rev. Immunol. 15:675-705.
18. Noble P. W., Barkauskas C. E., Jiang D., et al: Pulmonary fibrosis: patterns and perpetrators. J Clin Invest 2012; 122: 2756-2762.
19. Maher T. M.: Beyond the diagnosis of idiopathic pulmonary fibrosis: the growing role of systems biology and stratified medicine. Curr Opin Pulm Med 2013; 19: 460-465.

20. Shimbori C., Gauldie J., Kolb M., et al: Extracellular matrix microenvironment contributes actively to pulmonary fibrosis. Curr Opin Pulm Med 2013; 19: 446-452.
21. Raghu G, Collard H R, Egan J J, Martinez F J, Behr J, Brown K K, et al. An official ATS/ERS/JRS/ALAT statement: idiopathic pulmonary fibrosis: evidence-based guidelines for diagnosis and management. Am J Respir Crit Care Med 2011; 183(6):788-824.
22. Maher™. Pirfenidone in idiopathic pulmonary fibrosis. Drugs Today 2010; 46(7):473-482.
23. Bouros D. Pirfenidone for idiopathic pulmonary fibrosis. Lancet 2011; 377(9779):1727-1729.
24. Taniguchi H, Ebina M, Kondoh Y, Ogura T, Azuma A, Suga M, et al. Pirfenidone in idiopathic pulmonary fibrosis. Eur Respir J 2010; 35(4):821-829.

The invention claimed is:

1. A nucleic acid molecule encoding a humanized antibody that binds to at least two CCR3-binding chemokines wherein said nucleic acid molecule comprises the sequence denoted by SEQ ID NO: 1 and SEQ ID NO: 2.

2. An expression vector comprising the nucleic acid molecule of claim 1.

3. A host cell comprising the nucleic acid molecule of claim 1.

* * * * *

SEQUENCE LISTING

```
<160> NUMBER OF SEQ ID NOS: 19

<210> SEQ ID NO 1
<211> LENGTH: 360
<212> TYPE: DNA
<213> ORGANISM: Homo sapiens

<400> SEQUENCE: 1
cagatccaat tggtgcagtc tggacctgag ctgaagaagc ctggagcctc agtcaaggtc      60
tcctgcaggg cttctgggta tcccttcaca aactctggaa tgaactgggt aaagcaggct     120
ccaggaaagg gtttaaagtg gatgggctgg atcaacacct acaatggaga gccaacatat     180
actgatgact tcaagggacg gtttgccttc tctttggaaa cctctgccag cactgcctat     240
ttgcagatca acaacctcag aaatgaggac acggctacat atttctgtgc aagtcattcc     300
tacggtagta gctacgctat ggacaactgg ggtcaaggaa cctcagtcac cgtctcctca     360

<210> SEQ ID NO 2
<211> LENGTH: 333
<212> TYPE: DNA
<213> ORGANISM: Homo sapiens

<400> SEQUENCE: 2
gacattgtgc tgacccaatc tccagactct ttggctgtgt ctctagggga gagggccacc      60
atcaactgca aggccagcca aagtgttgat tatgatggtg atagttatat gaactggtac     120
caacagaaac caggacagcc acccaaactc ctcatctatg ttgcatccaa tctaaaatct     180
ggcatcccag ccaggtttag tggcagtggg tctgggacag acttcaccct caccatcagc     240
agcctgcagc ctgaggattt tgcaacctat tactgtcagc aaagtaatga ggaaccgtgg     300
acgttcggtg gaggcaccaa ggtggaaatc aaa                                  333

<210> SEQ ID NO 3
<211> LENGTH: 120
<212> TYPE: PRT
<213> ORGANISM: Homo sapiens

<400> SEQUENCE: 3

Gln Ile Gln Leu Val Gln Ser Gly Pro Glu Leu Lys Lys Pro Gly Ala
1               5                   10                  15

Ser Val Lys Val Ser Cys Arg Ala Ser Gly Tyr Pro Phe Thr Asn Ser
            20                  25                  30

Gly Met Asn Trp Val Lys Gln Ala Pro Gly Lys Gly Leu Lys Trp Met
        35                  40                  45

Gly Trp Ile Asn Thr Tyr Asn Gly Glu Pro Thr Tyr Thr Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Arg Asn Glu Asp Thr Ala Thr Tyr Phe Cys
                85                  90                  95
```

```
Ala Ser His Ser Tyr Gly Ser Ser Tyr Ala Met Asp Asn Trp Gly Gln
            100                 105                 110

Gly Thr Ser Val Thr Val Ser Ser
        115                 120

<210> SEQ ID NO 4
<211> LENGTH: 111
<212> TYPE: PRT
<213> ORGANISM: Homo sapiens

<400> SEQUENCE: 4

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Val Ala Ser Asn Leu Lys Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Glu Pro Trp Thr Phe Gly Gly Gly Thr Lys Val Glu Ile Lys
            100                 105                 110

<210> SEQ ID NO 5
<211> LENGTH: 5
<212> TYPE: PRT
<213> ORGANISM: Homo sapiens

<400> SEQUENCE: 5

Asn Ser Gly Met Asn
1               5

<210> SEQ ID NO 6
<211> LENGTH: 17
<212> TYPE: PRT
<213> ORGANISM: Homo sapiens

<400> SEQUENCE: 6

Trp Ile Asn Thr Tyr Asn Gly Glu Pro Thr Tyr Thr Asp Asp Phe Lys
1               5                   10                  15

Gly

<210> SEQ ID NO 7
<211> LENGTH: 11
<212> TYPE: PRT
<213> ORGANISM: Homo sapiens

<400> SEQUENCE: 7

His Ser Tyr Gly Ser Ser Tyr Ala Met Asp Asn
1               5                   10

<210> SEQ ID NO 8
<211> LENGTH: 15
<212> TYPE: PRT
<213> ORGANISM: Homo sapiens

<400> SEQUENCE: 8

Lys Ala Ser Gln Ser Val Asp Tyr Asp Gly Asp Ser Tyr Met Asn
```

<210> SEQ ID NO 9
<211> LENGTH: 7
<212> TYPE: PRT
<213> ORGANISM: Homo sapiens

<400> SEQUENCE: 9

Val Ala Ser Asn Leu Lys Ser
1               5

<210> SEQ ID NO 10
<211> LENGTH: 9
<212> TYPE: PRT
<213> ORGANISM: Homo sapiens

<400> SEQUENCE: 10

Gln Gln Ser Asn Glu Glu Pro Trp Thr
1               5

<210> SEQ ID NO 11
<211> LENGTH: 93
<212> TYPE: PRT
<213> ORGANISM: Homo sapiens

<400> SEQUENCE: 11

Val Val Ile Pro Ser Pro Cys Cys Met Phe Phe Val Ser Lys Arg Ile
1               5                   10                  15

Pro Glu Asn Arg Val Val Ser Tyr Gln Leu Ser Ser Arg Ser Thr Cys
                20                  25                  30

Leu Lys Ala Gly Val Ile Phe Thr Thr Lys Lys Gly Gln Gln Phe Cys
            35                  40                  45

Gly Asp Pro Lys Gln Glu Trp Val Gln Arg Tyr Met Lys Asn Leu Asp
        50                  55                  60

Ala Lys Gln Lys Lys Ala Ser Pro Arg Ala Arg Ala Val Ala Val Lys
65                  70                  75                  80

Gly Pro Val Gln Arg Tyr Pro Gly Asn Gln Thr Thr Cys
                85                  90

<210> SEQ ID NO 12
<211> LENGTH: 74
<212> TYPE: PRT
<213> ORGANISM: Homo sapiens

<400> SEQUENCE: 12

Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
                20                  25                  30

Lys Cys Pro Gln Lys Ala Val Ile Phe Lys Thr Lys Leu Ala Lys Asp
            35                  40                  45

Ile Cys Ala Asp Pro Lys Lys Lys Trp Val Gln Asp Ser Met Lys Tyr
        50                  55                  60

Leu Asp Gln Lys Ser Pro Thr Pro Lys Pro
65                  70

<210> SEQ ID NO 13
<211> LENGTH: 68
<212> TYPE: PRT
<213> ORGANISM: Homo sapiens -continued

<400> SEQUENCE: 13

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
            20                  25                  30

Lys Cys Ser Asn Pro Ala Val Val Phe Val Thr Arg Lys Asn Arg Gln
        35                  40                  45

Val Cys Ala Asn Pro Glu Lys Lys Trp Val Arg Glu Tyr Ile Asn Ser
50                  55                  60

Leu Glu Met Ser
65

<210> SEQ ID NO 14
<211> LENGTH: 76
<212> TYPE: PRT
<213> ORGANISM: Homo sapiens

<400> SEQUENCE: 14

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
50                  55                  60

Lys His Leu Asp Lys Lys Thr Gln Thr Pro Lys Leu
65                  70                  75

<210> SEQ ID NO 15
<211> LENGTH: 10
<212> TYPE: PRT
<213> ORGANISM: Homo sapiens

<400> SEQUENCE: 15

Cys Met Phe Phe Val Ser Lys Arg Ile Pro
1               5                   10

<210> SEQ ID NO 16
<211> LENGTH: 14
<212> TYPE: PRT
<213> ORGANISM: Homo sapiens

<400> SEQUENCE: 16

Cys Phe Asn Leu Ala Asn Arg Lys Ile Pro Leu Gln Arg Leu
1               5                   10

<210> SEQ ID NO 17
<211> LENGTH: 17
<212> TYPE: PRT
<213> ORGANISM: Homo sapiens

<400> SEQUENCE: 17

Ala Tyr Ile Ala Arg Pro Leu Pro Arg Ala His Ile Lys Glu Tyr Phe
1               5                   10                  15

Tyr

<210> SEQ ID NO 18
<211> LENGTH: 10
<212> TYPE: PRT

```
<213> ORGANISM: Homo sapiens

<400> SEQUENCE: 18

Cys Cys Tyr Arg Phe Ile Asn Lys Lys Ile
1               5                   10

<210> SEQ ID NO 19
<211> LENGTH: 9
<212> TYPE: PRT
<213> ORGANISM: Homo sapiens

<400> SEQUENCE: 19

Ser Tyr Arg Arg Thr Thr Ser Ser His
1               5
```